(12) United States Patent
Yun et al.

(10) Patent No.: US 11,576,571 B2
(45) Date of Patent: Feb. 14, 2023

(54) SYSTEMS AND METHODS FOR BRILLOUIN SPECTROSCOPY AND IMAGING OF TISSUES

(71) Applicant: THE GENERAL HOSPITAL CORPORATION, Boston, MA (US)

(72) Inventors: Seok-Hyun Yun, Belmont, MA (US); Amira Eltony, Jamaica Plain, MA (US)

(73) Assignee: The General Hospital Corporation, Boston, MA (US)

( * ) Notice: Subject to any disclaimer, the term of this patent is extended or adjusted under 35 U.S.C. 154(b) by 297 days.

(21) Appl. No.: 16/639,962

(22) PCT Filed: Aug. 20, 2018

(86) PCT No.: PCT/US2018/047074
§ 371 (c)(1),
(2) Date: Feb. 18, 2020

(87) PCT Pub. No.: WO2019/036714
PCT Pub. Date: Feb. 21, 2019

(65) Prior Publication Data
US 2020/0187771 A1    Jun. 18, 2020

Related U.S. Application Data

(60) Provisional application No. 62/547,171, filed on Aug. 18, 2017.

(51) Int. Cl.
*A61B 3/10*     (2006.01)
*A61B 3/117*    (2006.01)
(Continued)

(52) U.S. Cl.
CPC ............ *A61B 3/102* (2013.01); *A61B 3/1173* (2013.01); *A61B 5/0075* (2013.01); *G01J 3/0205* (2013.01);
(Continued)

(58) Field of Classification Search
None
See application file for complete search history.

(56) References Cited

U.S. PATENT DOCUMENTS 3,038,126 A    6/1962  Robison
3,807,390 A    4/1974  Ostrowski
(Continued)

FOREIGN PATENT DOCUMENTS

CN    104330398 A    2/2015
CN    104434028 A    3/2015
(Continued)

OTHER PUBLICATIONS

Akca, B.I. et al., "Observation of sound-induced corneal vibrational modes by optical coherence tomography," Biomedical optics express 6, 3313-3319 (2015).
(Continued)

*Primary Examiner* — Shawn Decenzo
(74) *Attorney, Agent, or Firm* — Quarles & Brady LLP

(57) ABSTRACT

Systems and methods are provided for measuring the mechanical properties of ocular tissue, such as the lens or corneal tissue, for diagnosis as well as treatment monitoring purposes. A laser locking feedback system is provided to achieve frequency accuracy and sensitivity that facilitates operations and diagnosis with great sensitivity and accuracy. Differential comparisons between eye tissue regions of a patient, either on the same eye or a fellow eye, can further facilitate early diagnosis and monitoring.

43 Claims, 16 Drawing Sheets

(51) Int. Cl.
| | |
|---|---|
| A61B 5/00 | (2006.01) |
| G01J 3/02 | (2006.01) |
| G01J 3/26 | (2006.01) |
| G01J 3/44 | (2006.01) |
| G01N 21/63 | (2006.01) |

(52) U.S. Cl.
CPC .............. *G01J 3/26* (2013.01); *G01J 3/4412* (2013.01); *G01N 21/636* (2013.01); *G01N 2021/638* (2013.01)

(56) References Cited

U.S. PATENT DOCUMENTS

| | | | | |
|---|---|---|---|---|
| 6,009,111 | A * | 12/1999 | Corwin | H01S 5/0687 372/27 |
| 7,898,656 | B2 | 3/2011 | Yun et al. | |
| 8,115,919 | B2 | 2/2012 | Yun | |
| 9,777,053 | B2 | 10/2017 | Yun | |
| 2012/0302862 | A1* | 11/2012 | Yun | A61B 3/1025 600/407 |
| 2013/0188141 | A1* | 7/2013 | Nakahara | G06T 7/73 351/246 |
| 2014/0368792 | A1 | 12/2014 | Friedman | |
| 2014/0368793 | A1* | 12/2014 | Friedman | A61B 3/107 351/221 |
| 2016/0059032 | A1* | 3/2016 | Skerl | A61F 9/0008 604/20 |
| 2016/0139390 | A1* | 5/2016 | Bukshtab | G02B 17/006 359/577 |
| 2016/0151202 | A1 | 6/2016 | Scarcelli | |
| 2016/0220110 | A1* | 8/2016 | Vogler | A61B 3/10 |

FOREIGN PATENT DOCUMENTS

| | | |
|---|---|---|
| GB | 975961 A | 11/1964 |
| JP | H11340557 A | 12/1999 |
| WO | 2008137637 A2 | 11/2008 |
| WO | 2014195949 A1 | 12/2014 |
| WO | 2014205145 A1 | 12/2014 |
| WO | 2017040959 A1 | 3/2017 |
| WO | 2017112896 A1 | 6/2017 |

OTHER PUBLICATIONS

Besner, S. et al., "In Vivo Brillouin Analysis of the Aging Crystalline Lens," Investigative ophthalmology & visual science 57, 5093-5100 (2016).

Bilaniuk N. et al., "Speed of sound in pure water as a function of temperature," The Journal of the Acoustical Society of America 93, 1609-1612 (1993).

Binder PS, et al. Keratoconus and corneal ectasia after Lasik J. Refractive Surg 2005;21(6):749-52.

Binder PS. Analysis of ectasia after laser in situ keratomileusis: Risk factors. J Cataract Refract Surg. 2007;33(9):1530-8.

Cusack S. et al., "Determination of the elastic constants of collagen by Brillouin light scattering," Journal of molecular biology 135, 39-51 (1979).

Dawson DG, et al. Corneal ectasia after excimer laser keratorefractive surgery: histopathology, ultrastructure, and pathophysiology. Ophthalmology. 2008;115(12):2181-91 e1.

Elsheikh A, et al. Comparative study of corneal strip extensometry and inflation tests. Journal of the Royal Society, Interface / the Royal Society. 2005;2(3):177-85.

Fontes BM, et al. Corneal biomechanical metrics in eyes with refraction of −19.00 to +9.00 D in healthy Brazilian patients. J Refract Surg. 2008;24(9):941-5.

Foster PJ, et al. Intraocular pressure and corneal biomechanics in an adult British population: the EPIC-Norfolk eye study. Investigative ophthalmology & visual science. 2011;52(11):8179-85.

Gal, O. et al., "Speed of Sound Measurement in Bovine Cornea at 35 MHz," Investigative ophthalmology & visual science 47, 1364-1364 (2006).

Gerstman D. R., "The biomicroscope and Vickers image splitting eyepiece applied to the diurnal variation in human central corneal thickness," Journal of microscopy 96, 385-388 (1972).

Girard, M.J. et al., "Translating ocular biomechanics into clinical practice: current state and future prospects," Current eye research 40, 1-18 (2015).

Goodfellow, J.M. et al., "X-ray diffraction studies of the corneal stroma," Journal of molecular biology 119, 237-252 (1978).

Harper C. L., et al., "Diurnal variations in human corneal thickness," The British journal of ophthalmology 80, 1068-1072 (1996).

Hatami-Marbini, H. et al., "Swelling pressure and hydration behavior of porcine corneal stroma," Current eye research 38, 1124-1132 (2013).

Hedbys B.O. et al., "The thickness-hydration relationship of the cornea," Exp Eye Res 5, 221-228 (1966).

International Searching Authority, International Search Report and Written Opinion for application PCT/US2018/047074, dated Jan. 22, 2019.

Kamiya K, et al. Effect of aging on corneal biomechanical parameters using the ocular response analyzer. J Refract Surg. 2009;25(10):888-93.

Leonard D. W. et al., "Refractive indices of the collagen fibrils and extrafibrillar material of the corneal stroma," Biophysical journal 72, 1382-1387 (1997).

Manchester, Jr. P.T., "Hydration of the cornea," Transactions of the American Ophthalmological Society 68, 425-461 (1970).

Mathieu, V. et al., "Micro-Brillouin scattering measurements in mature and newly formed bone tissue surrounding an implant," Journal of biomechanical engineering 133, 021006 (2011).

Meek, K.M. et al., "Changes in the Refractive Index of the Stroma and Its Extrafibrillar Matrix When the Cornea Swells," Biophysicical Journal 85, 2205-2212 (2003).

Meng, Z. et al., "Seeing cells in a new light: a renaissance of Brillouin spectroscopy," Advances in Optics and Photonics 8, 300 (2016).

Pallikaris IG, et al. Corneal ectasia induced by laser in situ keratomileusis. J Cataract Refract Surg. 2001;27:1796-802.

Polse KA, et al. Age differences in corneal hydration control. Investigative ophthalmology & visual science. 1989;30(3):392-9.

Rabinowitz YS. Ectasia after laser in situ keratomileusis. Current Opinion in Ophthalmology. 2006;17(5):421-426.

Roberts CJ, et al. Biomechanics of corneal ectasia and biomechanical treatments. J Cataract Refract Surg. 2014;40(6):991-8.

Saad A, et al. Biomechanical properties of keratoconus suspect eyes. Investigative ophthalmology & visual science. 2010;51(6):12912-6.

Scarcelli G, et al., "Confocal Brillouin microscopy for three-dimensional mechanical imaging," Nature photonics 2, 39-43 (2007).

Scarcelli G, et al. In vivo biomechanical mapping of normal and keratoconus corneas. JAMA ophthalmology. 2015; 133(4):480-2.

Silverman, R.H. et al., "Effect of corneal hydration on ultrasound velocity and backscatter," Ultrasound in medicine & biology 35, 839-846 (2009).

Spoerl E, et al. Cigarette smoking is negatively associated with keratoconus. J Refract Surg. 2008;24(7):S737-40.

Vellara HR, et al. Quantitative Analysis of Corneal Energy Dissipation and Corneal and Orbital Deformation in Response to an Air-Pulse in Healthy Eyes. Investigative ophthalmology & visual science. 2015;56(11):6941-7.

Ytteborg J. et al., "Corneal edema and intraocular pressure. II. Clinical results," Archives of ophthalmology (Chicago, Ill.: 1960) 74, 477-484 (1965).

* cited by examiner

SYSTEMS AND METHODS FOR BRILLOUIN SPECTROSCOPY AND IMAGING OF TISSUES

CROSS-REFERENCE TO RELATED APPLICATIONS

This application represents the national stage entry of PCT International Application No. PCT/US2018/0047074 filed Aug. 20, 2018, which claims the benefit of U.S. Provisional Patent Application Ser. No. 62/547,171 filed on Aug. 18, 2017, and entitled "APPARATUS FOR BRILLOUIN SPECTROSCOPY AND IMAGING OF TISSUES".

STATEMENT REGARDING FEDERALLY SPONSORED RESEARCH

N/A

BACKGROUND

The present disclosure relates to imaging of tissues. More particularly, the present disclosure relates to improved systems and methods for Brillouin spectroscopy and/or Brillouin microscopy.

The normal, healthy cornea typically has uniform elasticity throughout the volume of the corneal tissue. Corneal ectasia refers to a bulging of the cornea, occurring when it is not strong enough mechanically to withstand the intraocular pressure. Ectasia is one of the rare but serious adverse outcomes after LASIK (laser-assisted in situ keratomileusis) surgery, resulting in corneal thinning or weakening. Relatedly, pellucid marginal degeneration (PMD) is typically characterized by a thinning in the inferior and peripheral region of the cornea of one or both eyes. Similarly, keratoconus is a disorder characterized by thinning of the cornea. These and other conditions can be associated with local weakening or thinning of ocular tissue, and local differences in biomechanical properties such as elasticity. Biomechanical properties of ocular tissue may be an appropriate target for diagnosis and monitoring of onset and progression of cataract and presbyopia as well as corneal pathologies and treatments.

As evidenced by the above, the biomechanical properties of ocular tissues are implicated with several diseases and refractive treatments. Hence, various techniques have been developed for evaluating the biomechanical properties of ocular tissues.

However, the sensitivity and specificity of biomechanical measurements are often compromised by confounding factors. For example, the accuracy and sensitivity of air-puff based measurement of the corneal stiffness, using Scheimpflug topography or optical coherence tomography, can be substantially degraded by the influence of intraocular pressure (IOP), and in turn accurate measurement of IOP can be compromised by the coupling between IOP measurement and corneal stiffness.

In Brillouin imaging, the Brillouin scattering properties of tissue can be sensitive to the hydration level of the tissue. This can cause ambiguity in the interpretation of measured Brillouin shifts to the tissue's stiffness, as the diurnal variations and person-person difference in corneal hydration can lead to large variability that confuses clinical interpretation. The temperature of tissue is another confounding factor in Brillouin light spectroscopy. The Brillouin frequency shift from tissue can vary with the temperature. Therefore, Brillouin measurements conducted at a specific body temperature can give different values as compared with measurements at a different body temperature (e.g. due to fever), and this can lead to misinterpretation. For example, the temperature dependence of a tissue's Brillouin frequency shift can be about 7.45 MHz/° C. for an optical wavelength of 780 nm.

Of further concern, a Brillouin frequency sensitivity and accuracy of +/−10 MHz or better is required to distinguish subtle changes in the biomechanical properties of tissues or to detect abnormality in the early stage of disease. The accuracy of traditional Brillouin spectroscopy or microscopy systems can be significantly compromised by frequency drifts of freely running laser sources or temperature changes of the environment, which causes thermal mechanical shifts of components. For example, the frequency drift of a typical external-cavity semiconductor laser is about 100 MHz for a duration of 10 min even in a temperature-regulated room. Typically, the laser output contains a high level (−50 to −55 dB) of spontaneous background light relative to the stimulated emission laser line. This background noise is particularly a problem in Brillouin microscopy because back-reflected light from optical components or the tissue surface is configured to enter the Brillouin spectrometer and because of its broadband nature is difficult to separate from the weak Brillouin signal.

Hence, although currently existing biomechanical measurement techniques and systems can provide useful and valuable information for evaluating tissue in a patient, further improvements are desirable.

SUMMARY OF THE INVENTION

The present disclosure generally provides new and useful systems and methods for measuring the mechanical properties of tissue, such as the lens corneal tissue, for diagnosis as well as treatment monitoring purposes. In one aspect, the present disclosure uses a laser locking feedback system to achieve frequency accuracy and sensitivity that is superior to prior Brillouin spectroscopic or microscopic systems. In another aspect, new Brillouin imaging methods are provided that produce improved results using differential comparisons between eye tissue regions of a patient, either on the same eye or a fellow eye. In some cases, using unique human interface arrangements, biomechanical properties can be measured at any desired location (e.g. in x-y plane) and/or at any desired depth (e.g. along z axis) in the volume of the tissue.

In one aspect, the present disclosure provides a Brillouin spectroscopy system for evaluating a tissue in an eye tissue region of a patient. The system includes a laser source system comprising a tunable laser source configured to produce a first electromagnetic radiation having an electromagnetic spectrum and a vapor cell-based reference configured to capture a polarized form of a portion of the first electromagnetic radiation and provide an error signal containing information about a deviation of the electromagnetic spectrum from a target electromagnetic spectrum. The vapor cell-based reference includes a vapor cell configured to receive the portion of the first electromagnetic radiation and selectively transmit the portion of the first electromagnetic radiation based on the electromagnetic spectrum and a detector configured to receive the transmitted portion of the first electromagnetic radiation and produce the error signal. The Brillouin spectroscopy system also includes a human interface configured to direct the first electromagnetic radiation to the eye tissue region of the patient, wherein the first electromagnetic radiation generates at least one acoustic wave in the eye tissue region and at least one second electromagnetic radiation is produced based on the at least one acoustic wave. The Brillouin spectroscopy system further includes a spectrometer system configured to receive a portion of the second electromagnetic radiation and provide information associated with a biomechanical property of the eye tissue region.

In accordance with another aspect of the disclosure, a laser source system is provided for creating a laser with a stabilized peak frequency and filtered spontaneous emission noise. The laser source system includes a tunable laser source configured to produce a first electromagnetic radiation having an electromagnetic spectrum and a vapor cell-based reference configured to capture a polarized form of a portion of the first electromagnetic radiation and provide an error signal containing information about a deviation of the electromagnetic spectrum from a target electromagnetic spectrum. The vapor cell-based reference includes a first polarizer configured to receive and change the polarity of the portion of the first electromagnetic radiation, a vapor cell configured to receive the polarized form of the portion of the first electromagnetic radiation from the first polarizer, a second polarizer configured to receive the polarized form of the portion of the first electromagnetic radiation from the vapor cell and change the polarity of the portion of the first electromagnetic radiation, and a detector configured to receive the polarized form of the portion of the first electromagnetic radiation from the second polarizer and produce the error signal.

In accordance with another aspect of the disclosure, a method is provided for evaluating a tissue in an eye of a patient. The method includes obtaining a first biomechanical value for a first eye tissue region of the patient using Brillouin spectroscopy, obtaining a second biomechanical value for a second eye tissue region of the patient, and comparing the first biomechanical value with the second biomechanical value to determine a medical condition of the tissue of the eye of the patient.

In accordance with another aspect of the disclosure, a Brillouin spectroscopy system is provided for evaluating a tissue in an eye tissue region of a patient. The system includes a laser source system comprising a tunable laser source configured to produce a first electromagnetic radiation having an electromagnetic spectrum and a vapor cell-based reference configured to capture a portion of the first electromagnetic radiation and provide an error signal containing information about a deviation of the electromagnetic spectrum from a target electromagnetic spectrum, wherein the error signal is produced by monitoring the absorption of the first electromagnetic radiation by atoms within the vapor cell based reference. The Brillouin spectroscopy system also includes a human interface configured to direct the first electromagnetic radiation to the eye tissue region of the patient, wherein the first electromagnetic radiation interacts with at least one acoustic wave intrinsic to the eye tissue region and at least one second electromagnetic radiation is produced based on the at least one acoustic wave. The Brillouin spectroscopy system further includes a spectrometer system configured to receive a portion of the second electromagnetic radiation and provide information associated with a biomechanical property of the eye tissue region.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Aspects of the present disclosure encompass ophthalmic systems and methods that incorporate Brillouin light spectroscopy or other assessment techniques, for data acquisition, processing, and displaying biomechanical parameters. Exemplary tissue evaluation or assessment techniques that can be used in conjunction with the systems and methods disclosed herein include, without limitation, optical coherence tomography (OCT) modalities, Brillouin imaging modalities, Raman imaging modalities, laser speckle imaging modalities, multi-photon imaging modalities, photoacoustic imaging modalities, confocal microscopy imaging modalities, fluorescence imaging modalities, Pentacam imaging modalities, ultrasound imaging modalities, as well as approaches that combine or include one or more of these imaging modalities. Relatedly, exemplary tissue evaluation or assessment techniques that can be used in conjunction with the systems and methods disclosed herein, including those described in U.S. Pat. Nos. 7,898,656, 8,115,919, and 9,777,053, and U.S. Patent Publication Nos. 2012/0302862 and 2016/0151202, the contents of which are incorporated herein by reference.

Figure 1:
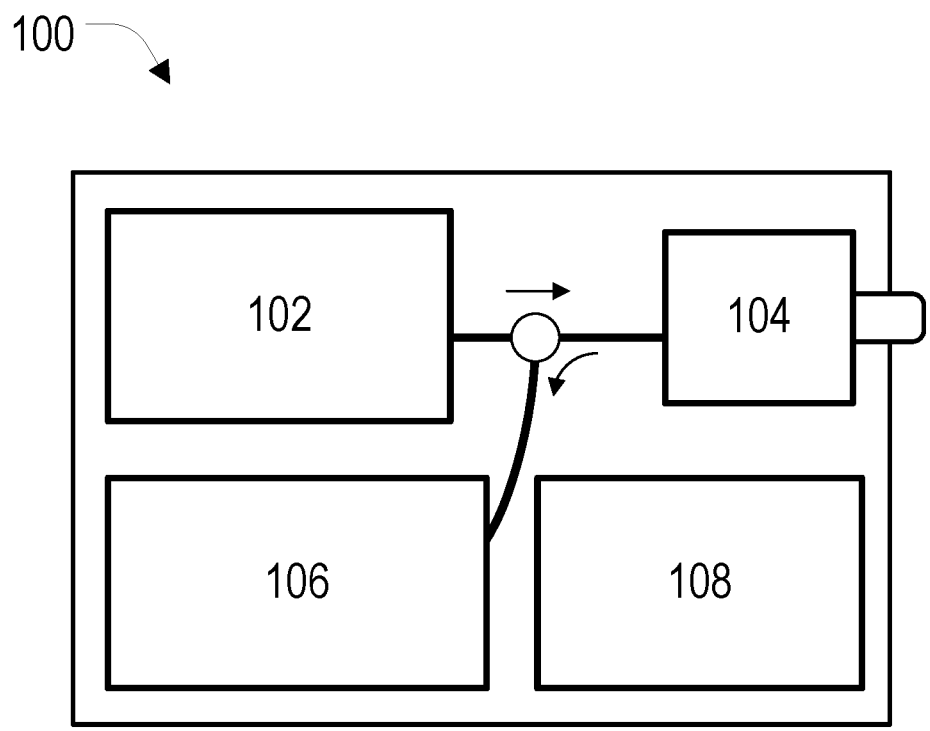
FIG. 1 is a block diagram of a Brillouin imaging system in accordance with the present disclosure.

FIG. 1 depicts a Brillouin imaging system 100 for evaluating biological tissues with improved measurement accuracy and reliability. The system, or apparatus, 100 may use Brillouin spectroscopy and/or Brillouin microscopy or a comparable Brillouin imaging technique. The system 100 advantageously improves signal filtering so that highly scattering tissues, such as the sclera, skin, and blood vessels, can be probed. The system 100 can comprise of a laser source system 102, a human interface 104, and a spectrometer system 106. In general, and without being bound by theory, the laser source system 102 produces electromagnetic radiation which may be directed at a biological tissue using the human interface 104. The electromagnetic radiation can generate a mechanical stress modulation in the tissue via thermal or electrostriction effects. When the stress modulation is phase-matched to one of the characteristic acoustic phonon modes in the tissue, the corresponding acoustic phonons can develop efficiently through a coherent process. The excited acoustic phonons in turn may create a refractive index modulation in the medium, and generate inelastic scattering of photons. The energy and momentum of the photons can be modified by an inelastic scattering procedure. The spectrometer system 106 may measure the scattered photons. Since the magnitude of a frequency shift in the scattered photons can be substantially or approximately equal to that of the acoustic phonons, biomechanical information of the tissue may be deduced. The system 100 may optionally comprise a computer system 108 capable of assisting with a number of functions, including but not limited to, processing information from the spectrometer 108 or providing feedback signals to the laser source system 102 or the human interface 104.

Laser Source System

The laser source system 102 may comprise a laser capable of emitting a narrowband spectrum locked to a specific absorption line, or target wavelength. The laser may have a stabilized peak frequency and filtered spontaneous emission noise. The absorption line may be an absorption line of an atomic species, such as the Rubidium absorption line at 780 nm. The laser may also comprise a vapor cell-based reference and/or a multi-stage spectral cleanup filter that may be locked to the output frequency of the laser.

Figure 2:
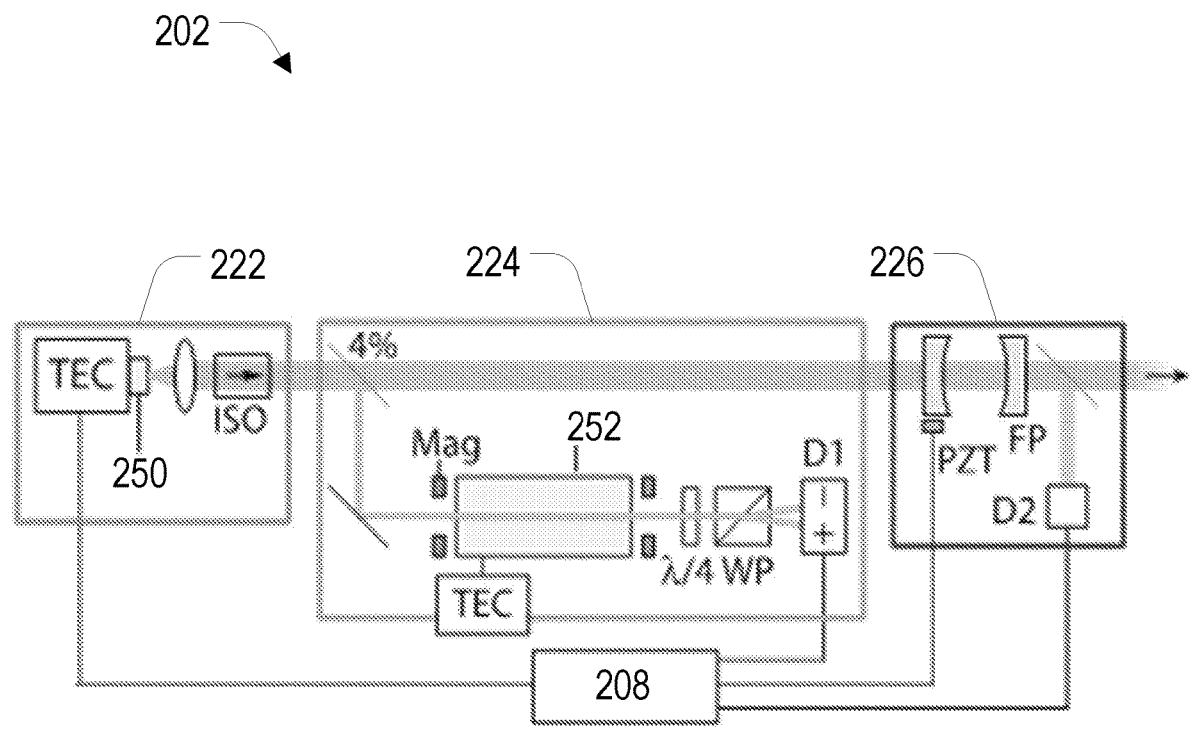
FIG. 2 is a block diagram of a laser source system in accordance with the present disclosure.

FIG. 2 is a schematic of a laser source system 202 optimized for Brillouin imaging. The laser source system 202 comprises a laser source 222, vapor cell-based reference 224, and a spectral cleanup filter 226. As illustrated therein the following abbreviations are used: thermoelectric controller (TEC), Wollaston prism (WP), balanced detector (D1), photodiode (D2), magnet (Mag), and piezoelectric transducer (PZT).

The laser source system can include a radiation emitting (e.g., light) source 250, which can be a single-frequency laser, a filtered Mercury lamp, or other types of light emitters known in the art. The source can have a wavelength between, e.g., about 530 nm and 1350 nm, although other wavelengths that are known to be safe for use in the eye can be used. The line width of the radiation can be typically less than about 1 GHz or more preferably less than about 100 MHz, although other light sources with broader line width or multiple spectral lines can be used in conjunction with appropriate arrangements. The radiation source 250 can utilize an optical arrangement to deliver more than one frequency line in order to enhance Brillouin scattered signal. The scattered radiation (e.g., light) from the sample can include multiple frequency components originated from simple elastic scattering as well as Brillouin scattering.

The light source 250 depicted is a single-frequency, distributed feedback (DFB) laser. However, the light source 250 used could be of a different type, such as a grating-based or external-cavity diode laser (ECDL). An integrated thermoelectric (ET) controller may be used to control the laser temperature. Because DFB lasers have higher temperature sensitivity than free-space ECDLs, it may be favorable to control the laser temperature to within about 0.01° C. through the use of such an integrated thermoelectric controller (TEC), which has a typical precision of near 0.001° C. If the laser is operating at a wavelength of about 780 nm, matching the absorption lines of rubidium (Rb) atoms, the output frequency may be locked to a transition peak of rubidium, as shown in the FIG. 2. For different laser wavelengths, other atom species may be used.

The vapor cell-based reference 224 may comprise a vapor cell filter 252 configured to receive a portion of the first electromagnetic radiation and selectively transmit the portion of the first electromagnetic radiation based on the electromagnetic spectrum. The vapor cell-based reference 224 may also comprise a detector configured to receive the transmitted portion of the first electromagnetic radiation and produce an error signal containing information about a deviation of the electromagnetic spectrum from a target electromagnetic spectrum. Alternatively, the vapor cell-based reference 224 may comprise alternative components capable of generating the error signal by monitoring the absorption of the source laser radiation by atoms in a small, unheated reference vapor cell. For example, instead of using the polarization-dependence of atomic absorption in a magnetic field, a small modulation may be added to the laser frequency. Although the portion captured is depicted as being 4% of the radiation produced by the light source 250, a smaller or larger captured portion may be used. The laser source system 202 may have a laser-lock setup based on atomic vapor lines that are essentially temperature independent. The version of the vapor cell depicted in FIG. 2 employs a laser lock technique that uses the Zeeman effect in the D2-line of $^{85}$Rb vapor atoms placed in a weak magnetic field.

In one aspect, the vapor cell-based reference 224 may include a first polarizer configured to receive and change a polarity of the portion of the first electromagnetic radiation, a vapor cell configured to receive the polarized form of the portion of the first electromagnetic radiation from the first polarizer, a second polarizer configured to receive the polarized form of the portion of the first electromagnetic radiation from the vapor cell and change the polarity of the portion of the first electromagnetic radiation, and a detector configured to receive the polarized form of the portion of the first electromagnetic radiation from the second polarizer and produce the error signal.

In FIG. 2 a polarized portion of the output from the laser 250 enters the vapor cell 252. Due to the presence of the weak magnetic field, the absorption curves of the two circular polarization components are shifted to higher and lower frequencies, respectively. After passing through the vapor cell 252, the beam may propagate through a quarter-wave plate and then the beam may propagate through a polarizing Wollaston prism. The dispersion-like curve generated from the difference between the two signals can provide an error signal for the frequency lock. This error signal may be sent to a computer system 208 which may then provide a signal to the thermoelectric controller of the laser source.

The frequency stability of an experimental vapor cell transition line was observed through experiments to be better than 2 MHz, and the laser frequency can be actively stabilized within +/−10 MHz using an analog servo control over a wide range of environmental temperatures typically from 15 to 25° C. Alternatively, frequency-locking to a solid etalon could also be employed, but the silica etalon as frequency reference is sensitive to temperature (about 3.8 GHz/° C.).

The spectral clean-up filter 226 may be locked to the output frequency of the laser and used to reduce spectral noise. The spectral clean-up filter 226 can comprise tandem, free-space, Fabry-Perot (FP) cavities, each comprised of a pair of concave mirrors. The mirrors may have a reflectivity of about 97%. The spectral clean-up filter may be designed to provide amplified spontaneous emission (ASE) suppression of about ~30 dB (per cavity) with a low insertion loss of between 1.5-3 dB. The spectral clean up filter may produce an ASE error signal. This error signal may be sent to a computer system 208 which may then provide a signal to the thermoelectric controller of the laser source. Each free-space cavity may be locked to the operating wavelength, or this may be achieved using a piezo-transducer (PZT). Frequency lock techniques, such as diter lock or a similar setup, may be used. The tandem FP cavities may have mismatched free spectral ranges so that background rejection is achieved over a wider spectral range around the laser peak. With mirror reflectivity near 90%, a rejection of near 20 dB may be achieved from each cavity with a low loss of below 0.5 dB. The extinction of the tandem cavities can thus be near 40 dB with loss below 1 dB. The frequency-locked laser combined with the clean-up filter may produce a high-purity output, for example, with a laser to noise level of greater than 80 dB.

The precision provided by the vapor cell-based reference 224 may be enhanced through using counter-propagating beams to obtain a narrower feature to lock to or through differential measurement with two beams, or the like. In one version of the laser source system 202, laser modulation may be used to generate both the laser locking and the cavity (ASE filter) locking error signals.

Human Interface

The human interface 104 serves as an intermediary between the output of the laser source system and the human subject, directing the produced electromagnetic energy towards the target tissue as intended. Additionally, the human interface 104 serves as an intermediary between the scattered electromagnetic radiation and the spectrometer system, ensuring that a portion of the scattered electromagnetic energy is measured.

In general, the output of the laser source system is delivered to the human interface and to a human subject. Scattered light from the human subject is collected in the human interface and is directed to a spectrometer for analysis. The scattered light contains not only Brillouin scattered signal but also background noise that has the same frequency spectrum as the probe laser. The noise is suspected of arising from two primary sources: reflection from various optical components in the system and elastic scattering from the tissue. For corneal imaging, Fresnel-type specular scattering at corneal surfaces is often orders of magnitude stronger than Brillouin scattering (at normal incidence, the corneal reflectivity is ~2%), so the specular reflection should be suppressed. In general, lenses used in the human interface are preferably anti-reflection coated and arranged such that the optical beam hits their surfaces at an angle and are tilted with respect to the optical path to minimize back reflection. Additionally, the probe beam axis can be tilted with respect to the normal axis of the corneal surface by about 15 degrees.

Figure 3A:
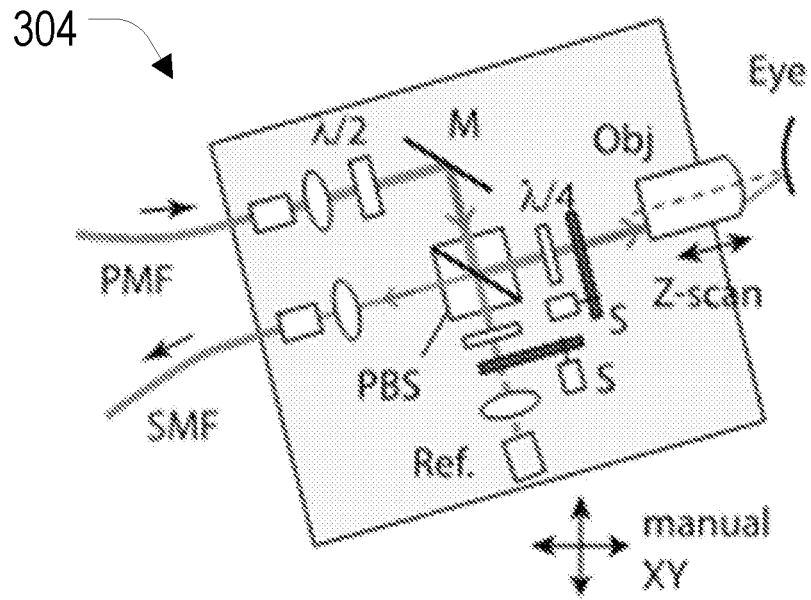
FIG. 3A is a schematic diagram depicting a two-fiber schematic of a human interface to be used in a Brillouin imaging system.

In the present disclosure, a rejection efficiency of about 65 dB is sufficient for corneal imaging. However, this marginal rejection efficiency constrains the choice of optical components and design of the human interface. As a result, one example system 304 of human interface has a bulky optical setup and requires that the beam enters the objective lens off axis, which can be seen in FIG. 3A. In the example system 304, the following abbreviations are used: polarization maintaining fiber (PMF); single mode fiber (SMF), mirror (M), motorized shutter (S), reference material (Ref). The off axis requirement precludes simple beam scanning in transverse directions (X and Y).

The angle of incidence may be greater than about 5 degrees to avoid excessive specular beam reflection from the tissue surface. Some tissues of layered microstructures, such as corneal tissues with rich collagen lamellas, have anisotropic properties. And as such, their Brillouin shift values depend on the tilt angle of the beam with respect to the tissue surface. The angular dependence can be considered in spectral analysis, and is a new source of information about collagen fiber orientation and structure, which is expected to change in disease. An angle-dependence metric may also be less sensitive to factors such as temperature and tissue hydration.

The high extinction of the Rb filter and VIPA etalon and the improved signal-to-background ratio of the laser source system allows one to construct a human interface with a 2×2 fiber-optic coupler or, alternatively, a fiber-optic circulator. The circulator replaces a bulky assembly of PBS, wave plates, and fiber-coupling optics. As shown in the example system 314 in FIG. 3B, a human interface can employ a 2-axis galvanometer mirror scanner and on-axis beam alignment. The single-fiber arrangement has a fiber-optic circulator and a beam scanner. The beam entrance angle to the tissue is tilted from the surface normal to avoid specular reflection. The system 314 adds a motorized flip mirror (FM) that can be controlled.

Conventional systems have reference materials with known Brillouin frequency shifts in their human interface and mechanical shutters to calibrate the measured Brillouin frequency shifts. The human interface may also have reference materials in a temperature-controlled mount. Alternatively, a temperature sensor may be attached to the reference materials, and the temperature-dependent Brillouin shifts of the reference materials are used for calibration. In another approach, an electro-optic frequency modulator (EOM) could be used to generate precise frequency side-bands on the laser for calibration of the spectrometer. One advantage of this technique is that by scanning the EOM frequency, a complete calibration curve can be generated, making it possible to correct for nonlinearities in the VIPA dispersion. Alternatively, for an Rb cell system, it may be possible to use the different transitions near 780 nm (e.g. the D2 transitions, which span 7-8 GHz) of the two abundant isotopes of Rb ($^{85}$Rb and $^{87}$Rb) as calibration points for the spectrometer.

For beam and eye tracking, an infrared light source and a monitoring camera can be used. To improve corneal surface profiling, structured light surface reconstruction can be added that uses the same monitoring camera with the addition of an LED pattern projector. A fluorescence dye, such as fluorescein, can be used as an image contrast agent. A custom beam registration software can be used with the computer system 108. Similarly, the computer system can be used to control the XY scanner using an algorithm based on the real-time images of the cornea. Z-scan can be achieved by the motorized translation of the objective lens. The user interface system can provide a uniform grid of scan points. Additionally, an enlarged field of view of can be provided to cover the cornea including the limbus. For example, the enlarged field of view may be about 8 mm×8 mm.

Figure 3B:
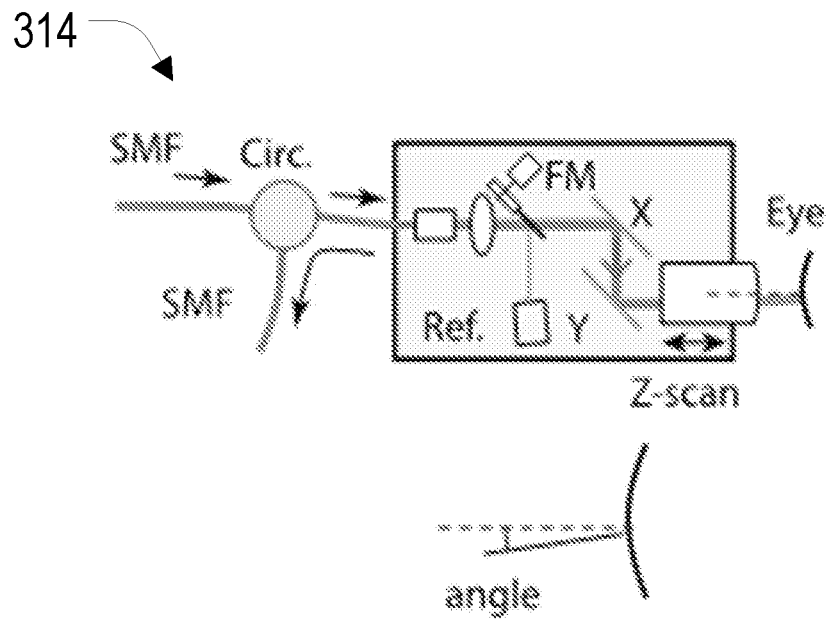
FIG. 3B is a schematic diagram depicting a single-fiber schematic of a human interface to be used in a Brillouin imaging system.
Figure 4:
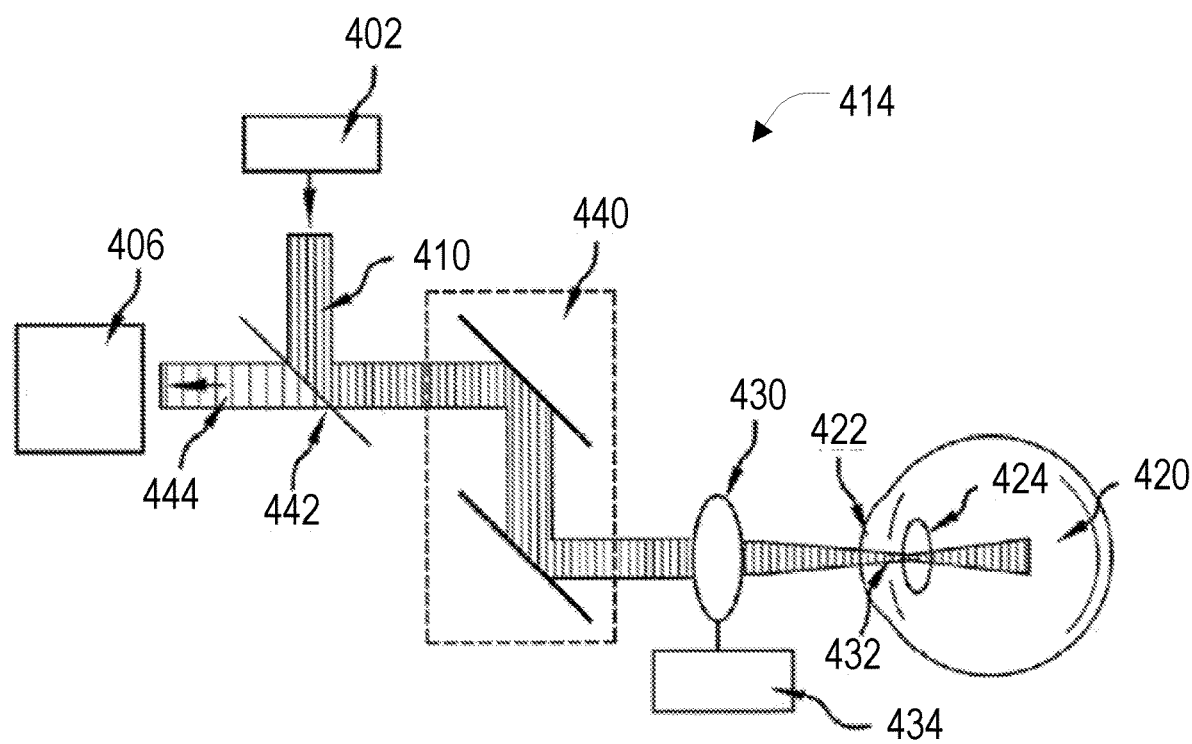
FIG. 4 is a block diagram that depicts the optical pathways for a single-fiber schematic of a human interface to be used in a Brillouin imaging system.

FIG. 4 illustrates a schematic of a version of the human interface 414 that presents the optical pathways of a system that corresponds to that presented in FIG. 3B. In this depiction, the laser source system 402 can provide a first electromagnetic radiation 410, which can be delivered to an eye 420. One exemplary form of the electromagnetic radiation 410 can be light in the visible or near infrared range. The electromagnetic radiation 410 can be directed to the eye 420 to probe various portions of ocular tissues, including but not limited to, cornea 422 and a crystalline lens 424. For example, an imaging lens 430 can be used to focus the electromagnetic radiation 410 onto a small eye tissue region. The imaging lens 430 can be a spherical convex lens, aspheric lens, objective lens, theta lens, or cylindrical lens for line focusing.

To scan the axial position of the focus within the ocular tissues, the imaging lens 430 can be mounted on a translation stage 434. Alternatively or in addition, a tunable element that can change a divergence of the probe radiation can be employed. To scan the transverse position of the focus, a one- or two-axis beam scanner 440 can be employed. The exemplary scanner 440 can include a galvanometer-mounted mirror, MEMS mirror, translation stages, spatial light modulator, and the like.

An acousto-optic interaction in the tissue can give rise to light/radiation scattering, thereby generating at least one second electromagnetic radiation. Several mechanisms for light/radiation scattering are known in the art, including Rayleigh and Mie scattering, Raman scattering, and Brillouin scattering. While biological tissues support these scattering mechanisms, Brillouin scattering is directly associated with the acoustic waves in the medium. A portion of such one or more second electromagnetic radiations can be collected by the imaging lens 430.

The exemplary system of FIG. 4 can utilize a beam splitter 442 to reflect and transmit the first and second electromagnetic radiations. The beam splitter 442 can have, e.g., an equal 50/50 splitting ratio or unequal splitting ratios for optimization of the efficiencies of signal generation and collection. The beam splitter 442 can be a neutral splitter with broad spectral bandwidth or a dichroic splitter based on multilayer coating, interference, or diffraction. The portion of the second electromagnetic radiation 444 can be transmitted to a second arrangement 406, which can be configured to receive the at least one portion 444 of such one or more second electro-magnetic radiations 444.

Figure 5A:
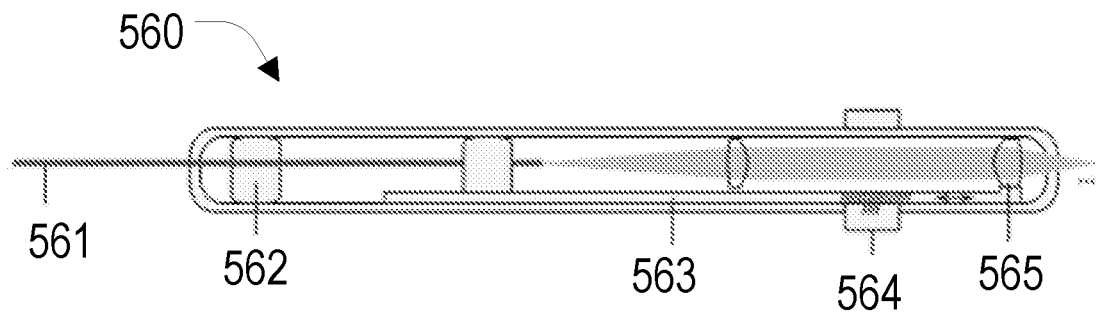
FIG. 5A is a schematic diagram of optical probe that forms a pen-type endoscope with a fixed focal length in accordance with the present disclosure.
Figure 5B:
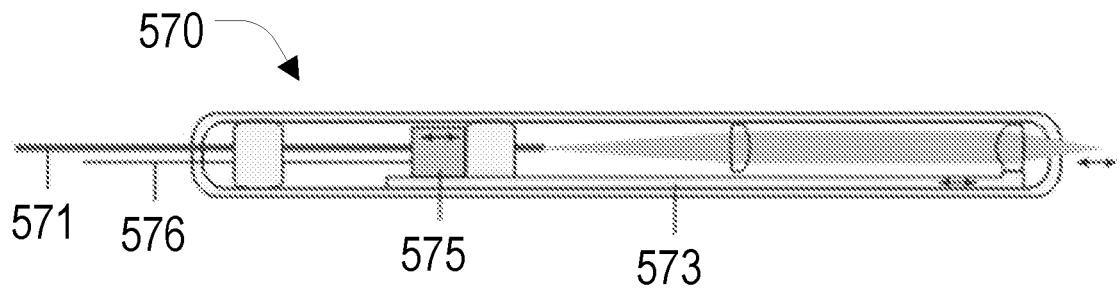
FIG. 5B is a schematic diagram of optical probe that forms an axis-tunable endoscope in accordance with the present disclosure.
Figure 5C:
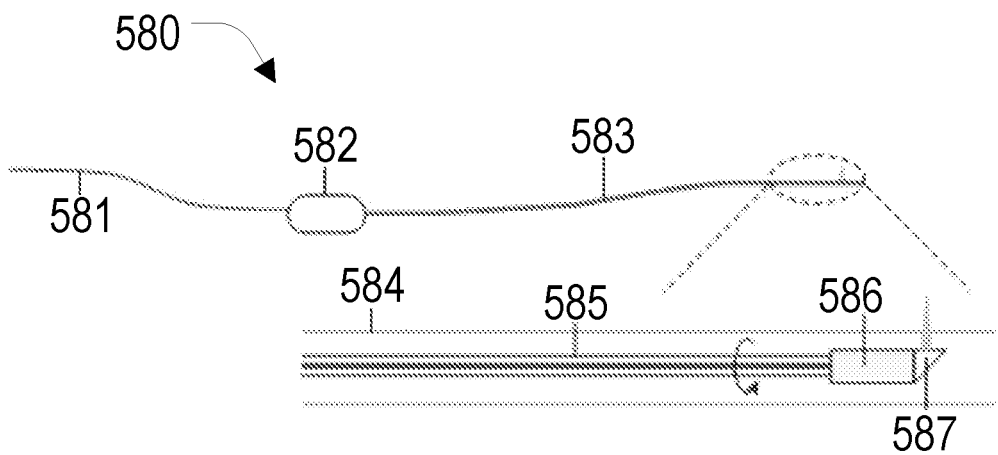
FIG. 5C is a schematic diagram of optical probe that forms a rotational catheter in accordance with the present disclosure.

Instead of the "table-top" setup depicted in FIGS. 3 and 4, the human interface may employ a fiber-optic probe in the form of an endoscope or catheter as depicted in the three arrangements of FIG. 5. The pen-type endoscope probe 560 in FIG. 5A comprises an optical fiber 561 held by a holder 562 and a focus control knob 564 configured to position a guide rail 563 in a manner that the electromagnetic radiation is properly produced from the lens 565 of the probe 560. The pen-type endoscope probe 570 of FIG. 5B has a similar construction to that of 560 but has a fixed focal length. The endoscope probe 570 has an optical fiber 571 and guide rail 573 but also has a voice coil 575 and a wire 576. The catheter probe 580 of FIG. 5C comprises an optical fiber 581 connected to a rotary junction 582 connected to a catheter 583. The catheter 583 is comprised of a sheath 584, a shaft coil 585 covering the optical fiber 583, a GRIN lens 586, and a mirror prism 587. Other comparable components or arrangements may be used.

The pen-type endoscopes depicted in FIGS. 5A and 5B may be used to interrogate the sclera noninvasively through the conjunctiva or to probe lens tissues behind the pupil during surgery. The catheter fiber-optic probe depicted in FIG. 5C may be used for intravascular measurement of the blood vessel wall or endoscopic interrogation of gastrointestinal tracts and airways. Fiber-optic probes integrated into needles may be used for identifying cancerous regions within a larger tissue mass. Fiber probes may have two separate optical fibers for the input and output ports, respectively, similar to FIG. 3A comprising two separate fibers. More preferably, endoscopes and catheters may have single fibers for both input and output ports. FIG. 5 illustrates three schematics of different versions of such optical probes. The probe can be directly coupled to the laser source system and the spectrometer fiber-optically. The probes may have two separate input and output fibers. However, it is possible and preferable to use a single fiber and realize the coupling to the laser source and spectrometer via an optical circulator, fiber-optic (2×2) splitter, or similar component.

In the single-fiber design, the optical fiber itself can generate spontaneous Brillouin scattering and the backward Brillouin scattered light can be combined with the Brillouin signal from a sample. Because the length of optical fiber can be as long as a few meters, the magnitude of Brillouin light generated from the optical fiber can be a few to several orders of magnitude larger than the magnitude of Brillouin light signal from the sample. For silica optical fibers, the Brillouin frequency shift is about 21-22 GHz for an optical wavelength of 780 nm. When this spectrum overlaps with the Brillouin spectrum of tissue, typically in 5-8 GHz, it is difficult to determine the tissue Brillouin shift accurately. Consequently, the system may have a spectrally resolving arrangement to remove the fiber-origin Brillouin light or separate the two Brillouin spectra from each other. In one version, a VIPA etalon with a FSR equal to the Brillouin shift of the optical fiber (e.g. 21-22 GHz), or a half or 1.5 times of it, such that the fiber-origin Brillouin spectrum overlaps with the background spectrum due to reflection of laser light or elastic scattering and is separated from the Brillouin signal spectrum from the sample.

Additionally or alternatively, a non-reciprocal polarization rotator may be employed at the distal end of the lead fiber before the sample so that the fiber-origin Brillouin scattered light and the sample-origin Brillouin scattered light have orthogonal polarization states. Then, a polarization beam splitter can be employed in the proximal end of the lead fiber to direct only the sample-origin Brillouin signal to the spectrometer.

Spectrometer

The spectrometer system 106 may be of any known type that is suitable to function with the chosen laser source system and human interface. The spectrometer system 106 may be configured to receive a portion of the scattered electromagnetic radiation and provide information associated with a biomechanical property of the animal tissue.

Figure 6:
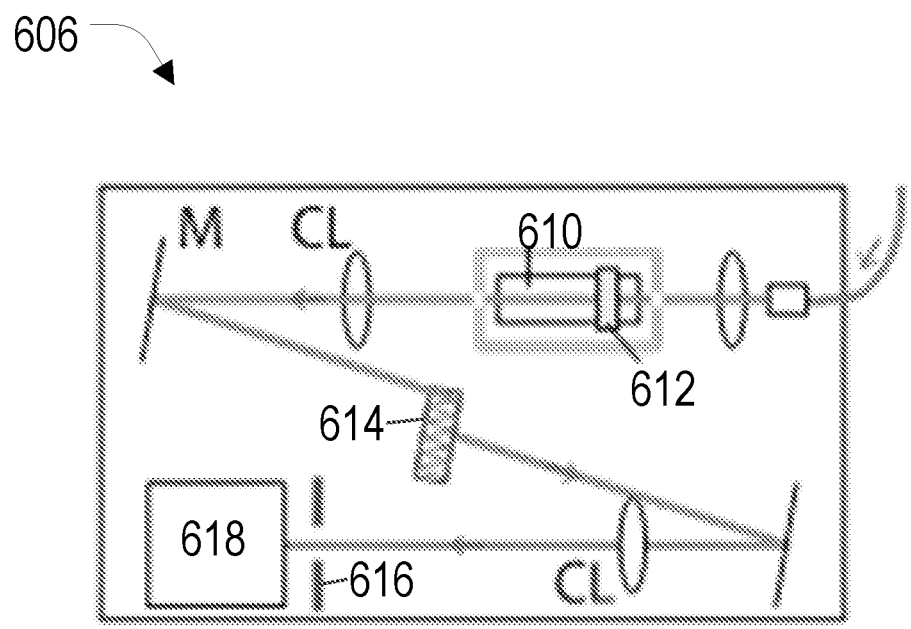
FIG. 6 is a schematic diagram of a spectrometer with an Rb vapor absorption filter and a single-stage VIPA etalon in accordance with the present disclosure.

FIG. 6 depicts a version of the spectrometer system 606 that employs a Rubidium vapor absorption filter to attenuate the laser frequency component while transmitting Brillouin scattered light with low insertion loss. The system includes an Rb cell 610 with a heater 612, cylindrical lens (CL), mirrors (M), a VIPA etalon 614, a mask 616, and a charge coupled device (CCD) 618 as a detector. The spectrometer system 606 can further employ calibration devices, which may be temperature-stabilized calibration materials or an electro-optic frequency modulator to generate side-bands for precise calibration of the spectrometer.

Conventional systems have used two VIPA etalons in two stages. The optical insertion loss of the second stage is typically 5-6 dB, higher than 3-4 dB loss in the first stage. With sufficient rejection, an Rb notch filter allows us to use only one VIPA stage. With a typical single-stage extinction of 30-40 dB, the combined extinction of the rejection filter and VIPA is greater than 90 dB. The single-stage design can reduce the size, complexity, cost, and importantly, the optical loss. Also, it allows for line scanning or a simultaneous detection and readout from a fiber bundle.

Figure 7:
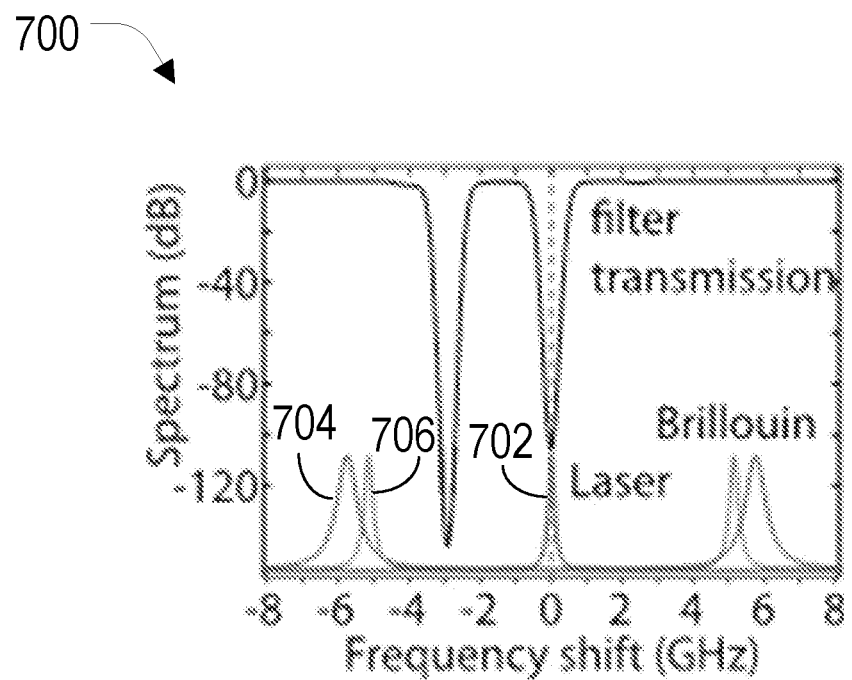
FIG. 7 is a graph that depicts an attenuation spectrum (black) of a 10-cm-long Rb vapor cell at a vapor pressure of 9 µPa (65° C.) and the spectra of the laser signal to be rejected (702, amplitude not to scale) and the approximate signals from corneal stroma (704) and the aqueous humor (706, amplitude not to scale).

In the detection path, a high-vapor pressure Rb absorption filter can be employed to remove Fresnel reflected and Rayleigh scattered light from the light collected from the human interface with high extinction. The Rb notch filter can remove the spurious elastic components, which have the same frequency as the laser line, from the light before it enters a spectrometer, such as the VIPA etalon spectrometer depicted. A multi-pass FP etalon-based filter can give an extinction as high as 40 dB, but can have reduced mechanical stability and high sensitivity to temperature. As illustrated in the attenuation spectrum of FIG. 7, experimental results showed that the high-pressure Rb vapor cell filter can provide much higher single-pass rejection of greater than 60 dB or even greater than 80 dB when the Rb gas is heated at 65° C. in an insulated oven. The insertion loss of the vapor absorption filter may be less than 1 dB. The high-pressure Rb vapor cell filter is intrinsically compatible with an Rb laser source with its frequency locked to the same transition line of Rb atoms.

The spectrometer system 606 of FIG. 6 can include a low-cost, thermos-electrically cooled CCD camera, instead of more expensive EM-CCD camera. For example, commercially available cameras developed for astronomy applications have a high quantum efficiency of 65% at 780 nm and a low readout noise of about 3-6 electrons. A frequency measurement sensitivity of around 10 MHz requires about 1,000 signal electrons total over several pixels. When the number of Brillouin signal photon exceeds 56 photons (36 electrons) per pixel, shot noise is greater than the readout noise. The signal-to-noise ratio (SNR) penalty due to the readout noise and slightly lower quantum efficiency is less than 3 dB. Experimental results have shown that the signal increase of about 5-6 dB gained by removing the second VIPA stage is sufficient to counteract the readout noise penalty (less than 3 dB) by the readout noise and the insertion loss (1 dB) of the rejection filter, so that the overall system's detection sensitivity is not compromised but possibly enhanced.

Conventional systems have used VIPA etalons made of fused silica with a temperature-dependent refractive index (10-5/° C.). With silica etalons, the diffraction pattern on a CCD can shift by 3.8 GHz/° C. as a function of the environmental temperature; such a temperature sensitivity would likely only be acceptable in a temperature-regulated lab environment where the shift tends to be slow enough (e.g. <10 MHz/min or <2.6×10-3° C./min) so that it can be corrected by the calibration using reference material in the human interface. However, the temperature sensitivity must be improved for use in more general settings. To solve this problem, the spectrometer 606 uses VIPA etalons made of ultralow-expansion (ULE) glass, such as Zerodur, which has a thermal expansion coefficient of about $5 \times 10^{-9}$/° C. The ULE VIPA etalons will have 2,000 times lower temperature sensitivity than silica VIPA etalons, eliminating calibration errors for temperature slopes of up to 5.2° C./min. In addition, or alternatively, a small heater and TEC may be used to stabilize the temperature of either ULE or silica etalons.

Computer System

The computer system 108 may be electrically or wirelessly connected to the laser source system 102, the human interface 104, the spectrometer system 106, and/or any additional components of the Brillouin imaging system. The computer system 108 may be used to provide feedforward or feedback control while Brillouin imaging system 100 is in use. In this manner the computer system 108 may affect the output of the laser source system and/or modify a human interface parameter, such as angle of incidence, in real-time.

Figure 8:
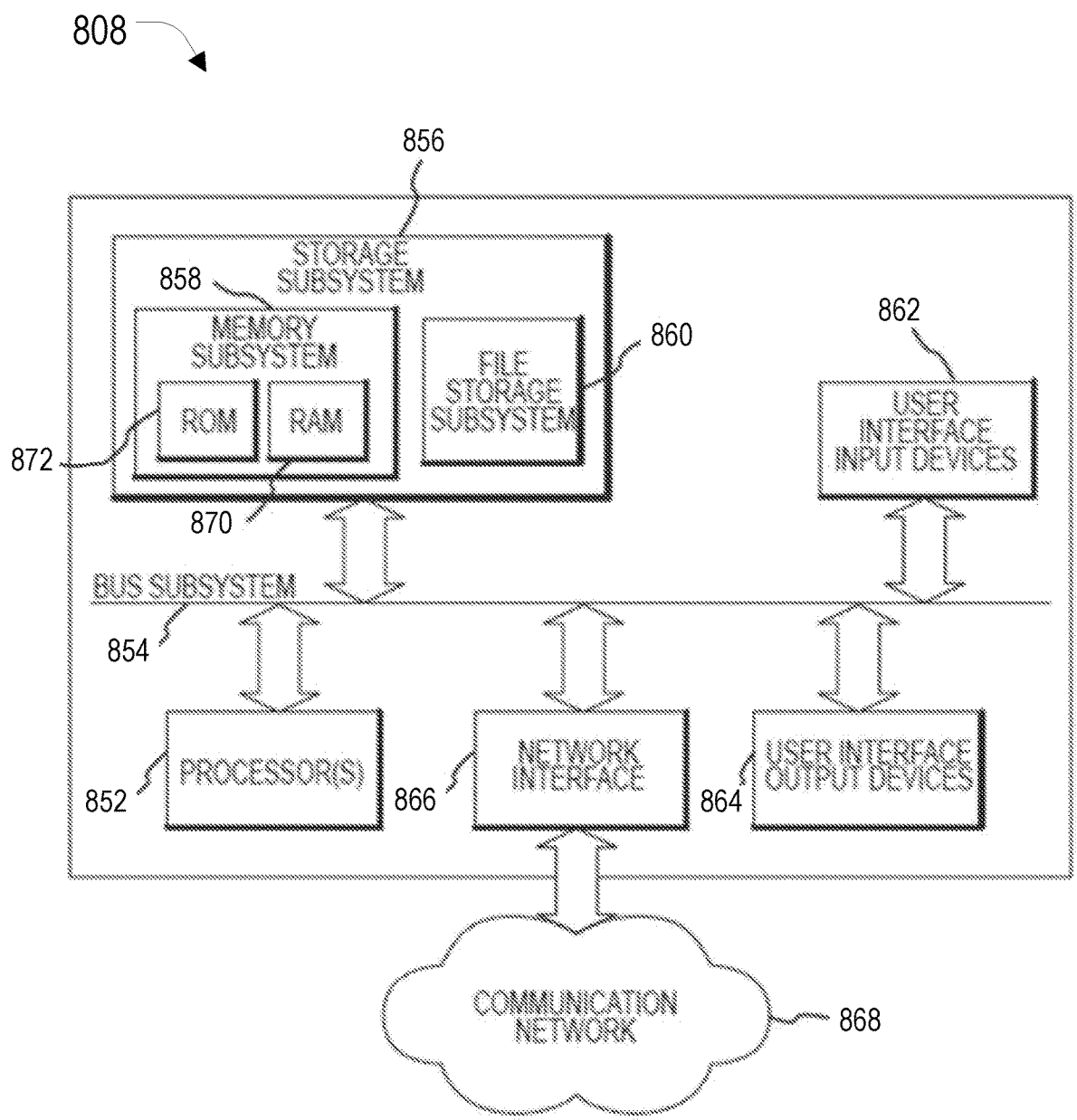
FIG. 8 is a simplified block diagram of an exemplary computer system that may be used with a Brillouin imaging system in accordance with the present disclosure.

FIG. 8 is a simplified block diagram of a computer system 808 that may be used Brillouin imaging system of the present disclosure. The computer system 808 typically includes at least one processor 852 which may communicate with a number of peripheral devices via a bus subsystem 854. These peripheral devices may include a storage subsystem 856, comprising a memory subsystem 858 and a file storage subsystem 860, user interface input devices 862, user interface output devices 864, and a network interface subsystem 866. Network interface subsystem 866 provides an interface to outside networks 868 and/or other devices, such as the tissue evaluation system.

User interface input devices 862 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User input devices 862 will often be used to download a computer executable code from a tangible storage media embodying any of the methods of the present invention. In general, use of the term "input device"

is intended to include a variety of conventional and proprietary devices and ways to input information into computer system 808.

User interface output devices 864 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 808 to a user.

Storage subsystem 856 can store the basic programming and data constructs that provide the functionality of the various aspects of the present disclosure. For example, a database and modules implementing the functionality of the methods of the present invention, as described herein, may be stored in storage subsystem 856. These software modules are generally executed by processor 852. In a distributed environment, the software modules may be stored on a plurality of computer systems and executed by processors of the plurality of computer systems. Storage subsystem 856 typically comprises memory subsystem 858 and file storage subsystem 860.

Memory subsystem 858 typically includes a number of memories including a main random access memory (RAM) 870 for storage of instructions and data during program execution and a read only memory (ROM) 872 in which fixed instructions are stored. File storage subsystem 860 provides persistent (non-volatile) storage for program and data files, and may include tangible storage media which may optionally embody tissue evaluation data. File storage subsystem 860 may include a hard disk drive, a floppy disk drive along with associated removable media, a Compact Disc Read Only Memory (CD-ROM) drive, an optical drive, DVD, CD-R, CD-RW, solid-state removable memory, and/or other removable media cartridges or disks. One or more of the drives may be located at remote locations on other connected computers at other sites coupled to computer system 808. The modules implementing the functionality of the methods of the present disclosure may be stored by file storage subsystem 860.

Bus subsystem 854 provides a mechanism for letting the various components and subsystems of computer system 808 communicate with each other as intended. The various subsystems and components of computer system 808 need not be at the same physical location but may be distributed at various locations within a distributed network. Although bus subsystem 854 is shown schematically as a single bus, alternate embodiments of the bus subsystem may utilize multiple busses.

Computer system 808 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 808 depicted in FIG. 8 is intended only as a specific example for purposes of illustrating one aspect of the present disclosure. Many other configurations of computer system 808 are possible having more or less components than the computer system depicted in FIG. 8.

Differential Method

The differential method described herein can be used with the improved Brillion imaging systems described above or with traditional systems in order to better evaluate the tissue of an eye of a patient.

It has been discovered that many confounding factors affect the biomechanical properties of the tissue globally, whereas the biomechanical information of interest can manifest itself locally. For example, temperature affects the entire cornea rather uniformly, whereas the pathological changes due to keratoconus can occur heterogeneously or in a spatially dependent manner.

It is possible to evaluate a patient using a differential metric that is based on changes in elasticity within the cornea (e.g. by considering the difference in elasticity between the thinnest point of the cornea and the central point of the cornea), or that is based on a difference in corneal elasticity between the two eyes of the patient. The thinnest point of the cornea can be identified by various methods, including corneal topography approaches that identify the steepest curvature of the cornea. Pachymetry can also be used to identify the thinnest point of the cornea. Once obtained, these differential elasticity values can be used, instead of using absolute elasticity values, which may vary widely and overlay between a normal healthy population and a keratoconus, or otherwise damaged, population. Keratoconus is typically a bilateral disease with a differential in onset time between two eyes. Exemplary differential metrics have a desirable sensitivity-specificity in the differentiation of normal versus abnormal corneas.

In one aspect, the present disclosure provides methods for measuring differences of biomechanical properties between two eye tissue regions and generating metrics based on the differences. By taking the differences into account, the homogeneous contribution of confounding factors can be reduced or canceled out and, therefore, the errors in the interpretation of the measurement can be reduced or removed. Consequently, the systems and methods can employ metrics which improve the detection of desirable biomechanical information of tissues, which may be otherwise obscured by the confounding factors.

Figure 9:
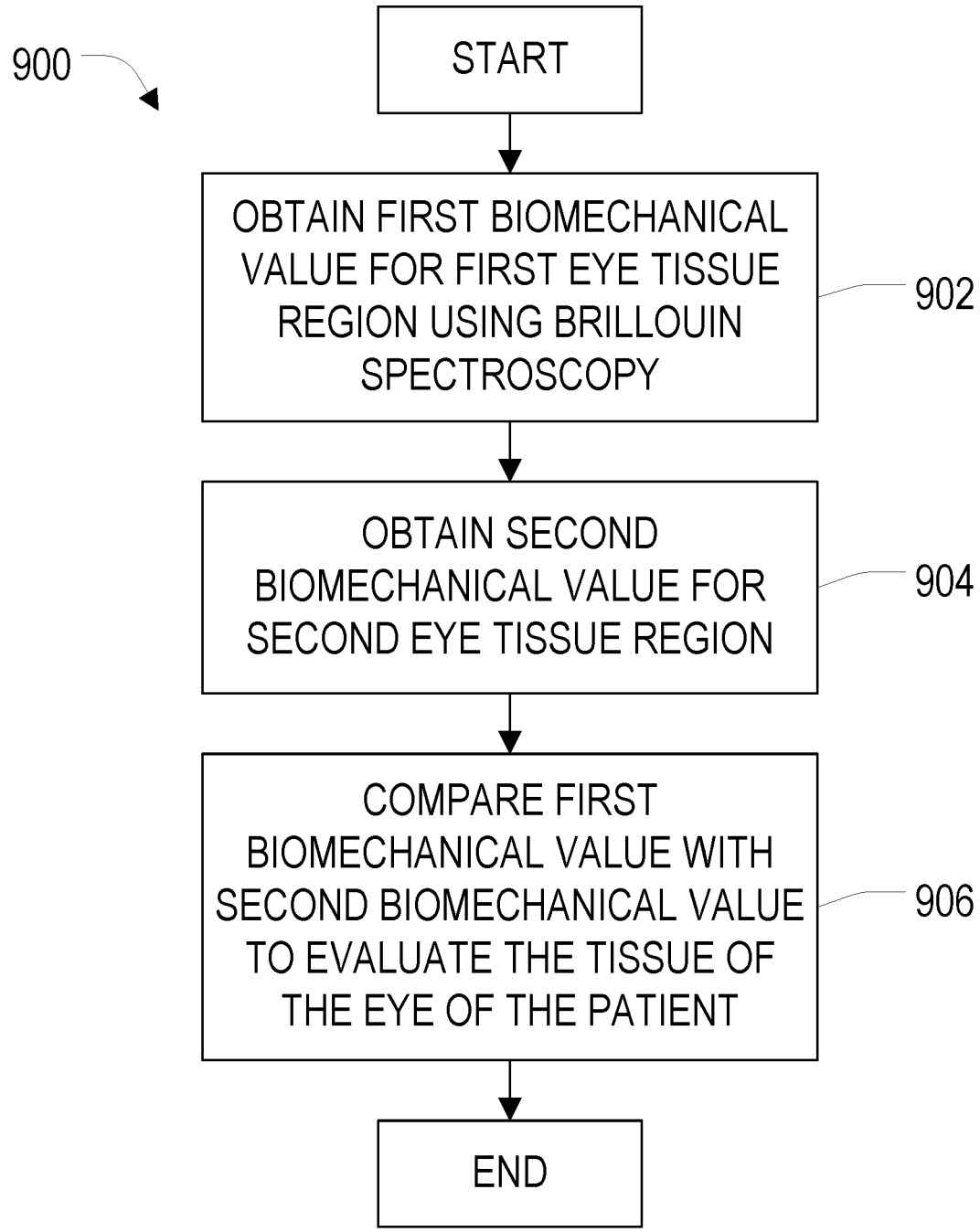
FIG. 9 is a flowchart setting forth some examples of non-limiting steps of a method of evaluating a tissue in an eye of a patient in accordance with the present disclosure.

FIG. 9 depicts a process flowchart 900 for a differential method, wherein a first biomechanical value for a first eye tissue region is obtained using Brillouin spectroscopy 902, a second biomechanical value for a second eye tissue region is obtained 904, and the first biomechanical value is compared with the second biomechanical value to evaluate the tissue of the eye of the patient 906.

Binocular Evaluation

Symmetry between the two healthy eyes of the same individual is well-documented, including symmetry in the distribution of biomechanical properties in the human cornea. Studies with X-ray scattering techniques reveal that in the stroma, which is about 90% of the thickness of the cornea, collagen fibers are arranged in a highly anisotropic manner and are preferentially aligned in a pattern. The structure is symmetric between the two eyes. This results in a symmetric biomechanical property distribution in the two corneas of one individual.

In a binocular approach, methods for evaluating a tissue in an eye of a patient can include obtaining a first biomechanical value for a first eye tissue region of the patient; obtaining a second biomechanical value for a second eye tissue region of the patient; and comparing the first biomechanical value with the second biomechanical value to evaluate the tissue of the eye of the patient, wherein the first tissue region is located on the eye of the patient and the second tissue region is located on a fellow eye of the patient. The biomechanical value may be an elasticity value. The first and second tissue regions may each be selected from the selected from the group consisting of a corneal tissue, a sclera tissue, and a lens tissue.

Put another way, exemplary methods can involve a step to obtain biomechanical values from both eyes, followed by a step to generate metrics related to the difference of the biomechanical values between the left and right eyes. The second biomechanical value may be obtained from Brillouin spectroscopy or Brillouin microscopy. Alternatively, the second biomechanical value may be obtained by using air-puff based optical imaging, such as Scheimpflug topography or optical coherence tomography, and the biomechanical values may be related to air-puff induced deformation of the corneas.

Monocular Evaluation

In a monocular approach, methods for evaluating a tissue in an eye of a patient can include obtaining a first biomechanical value for a first eye tissue region of the patient; obtaining a second biomechanical value for a second eye tissue region of the patient; and comparing the first biomechanical value with the second biomechanical value to evaluate the tissue of the eye of the patient, wherein the first tissue region and the second tissue region are located on the eye of the patient. The biomechanical value may be an elasticity value. The first and second tissue regions may each be selected from the selected from the group consisting of a corneal tissue, a sclera tissue, and a lens tissue.

In all studied keratoconus patients from stage 1 to 4, the Brillouin shift values measured in the cone areas were significantly (P<0.05) lower than the values in the peripheral regions (3 mm away from the optic axis) in the same eyes. By comparison, the Brillouin shift values at the cone regions in keratoconus patients were not highly distinctly different (p>0.05) from those measured in normal subjects at the central corneas, presumably because of the relatively large variability between subjects.

The above successful examples based on comparing the left and right eyes of each subject and comparing regional difference within the same cornea represent the usefulness of "self-calibration", where the calibration reference is provided by another region in the same eye or the other eye of the subject.

EXAMPLES

The following examples are provided in order to demonstrate and further illustrate certain embodiments and aspects of the present disclosure and are not to be construed as limiting the scope of the disclosure.

Example 1

A study was conducted to evaluate the efficacy of the systems and methods described herein as well as the confounding factors that necessitate these solutions.

Figure 10:
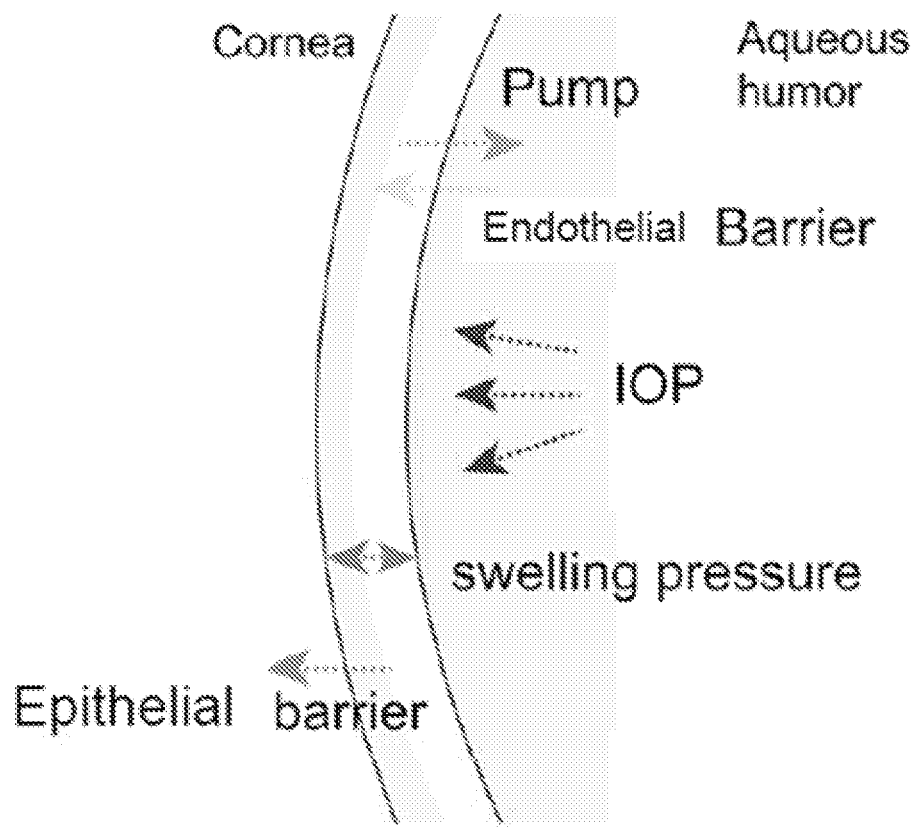
FIG. 10 is a schematic illustration that depicts various components of a human eye near the cornea as well as pressure and diffusion arrows.

Corneal hydration is a dynamic equilibrium, maintained or affected by several confounding factors shown in FIG. 10, with diurnal variations due to environmental and physiological changes. Normal water content of the cornea can be kept constant by a balance of factors that draw water into the cornea (e.g. swelling pressure and intraocular pressure), that prevent water flow in the cornea (e.g. epithelial barrier), and that draw water out of the cornea (e.g. endothelial pump).

In clinical terms, a change in corneal hydration can be indirectly estimated by using the central corneal thickness (CCT), because the cornea swells perpendicularly to the tangent direction. An increase in CCT suggests higher water content, compromised elasticity, and thus causes a decreased Brillouin frequency shift. In the study, diurnal changes in CCT and corresponding Brillouin frequency shifts in central corneas were measured, and this trend was confirmed.

Figure 11:
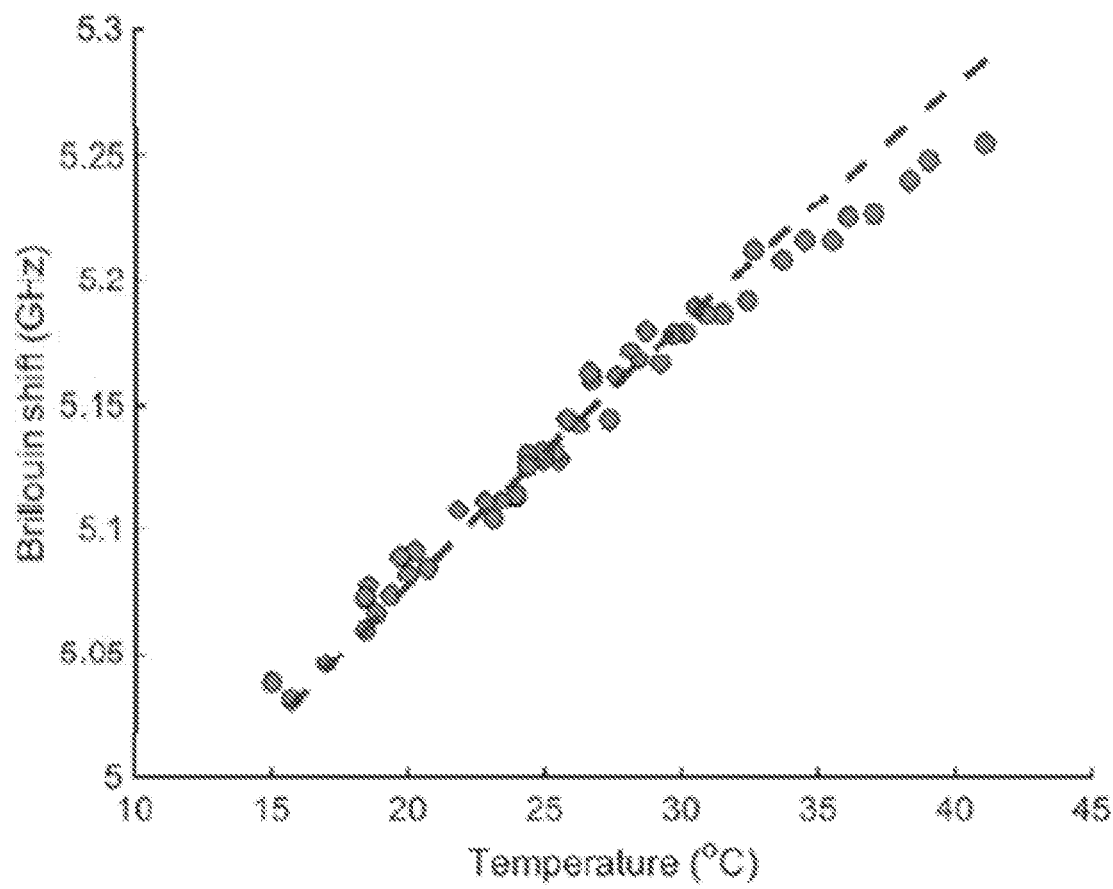
FIG. 11 is a graph that depicts experimentally measured Brillouin frequency shifts at 780 nm in pure water in a temperature window from 15-40° C.

Temperature is another confounding factor in Brillouin light spectroscopy. FIG. 11 shows experimentally measured Brillouin frequency shifts at 780 nm in pure water in a temperature window from 15-40° C. The dots represent raw data, and the dashed line represents a fitted second order polynomial. The temperature dependence of corneal tissue is similar to water, about 5 MHz/° C. The corneal temperature is known to vary among individuals with some correlation with age and daily physiological status. At room temperature, the corneal temperature is lower than body temperature by a few to several degrees because of heat transfer to the ambient air. Therefore, the ambient temperature also affects the corneal temperature. The Brillouin imaging system of the present disclosure may therefore incorporate a temperature measuring device, such as an infrared detector, to measure the temperature of the cornea and to correct for the temperature dependence. A thermometer to measure ambient temperature may also be included to estimate the corneal temperature using simple thermal modeling of the eye.

Diurnal variations of Brillouin measurements and corneal hydration (CCT) measurements in the central cornea were evaluated in healthy subjects. FIG. 11A shows the diurnal variations in Brillouin frequency shift and CCT measurements from a healthy subject. The left column depicts raw data taken throughout the day from ~1 hour after waking up. The right column depicts the difference between the two eyes in Brillouin shift and CCT measurements. The results showed a very small difference between the two eyes for both measurements, within the system errors (<+/−10 MHz, and <10 μm).

Figure 12A:
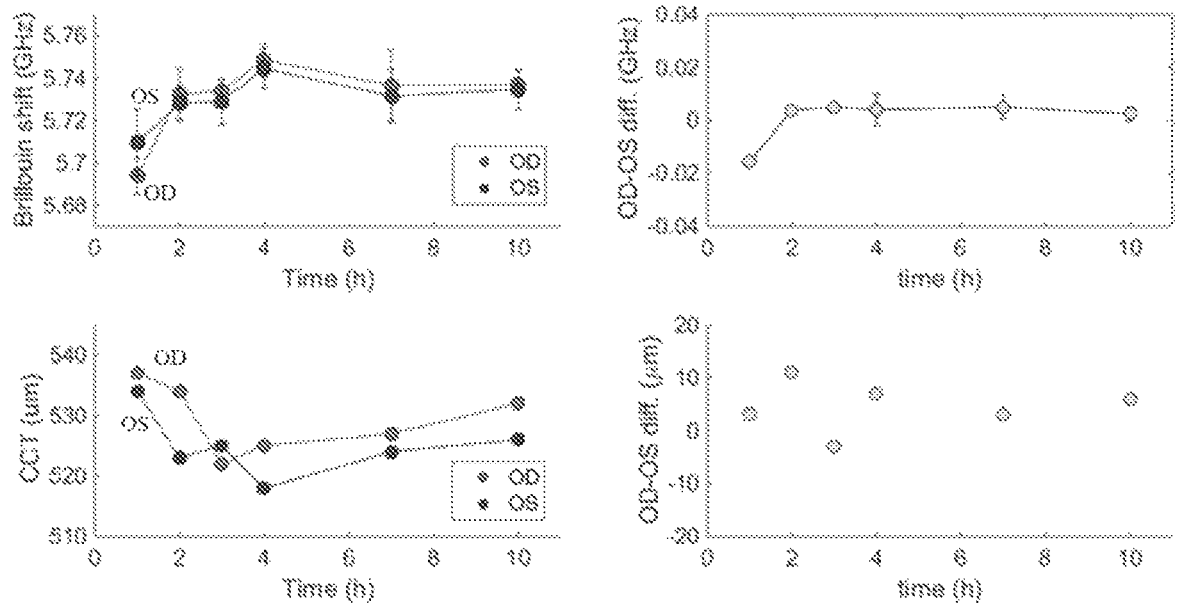
FIG. 12A is a set of correlated graphs that depict experimental results of measured diurnal variations in Brillouin frequency shift and CCT measurements.
Figure 12B:
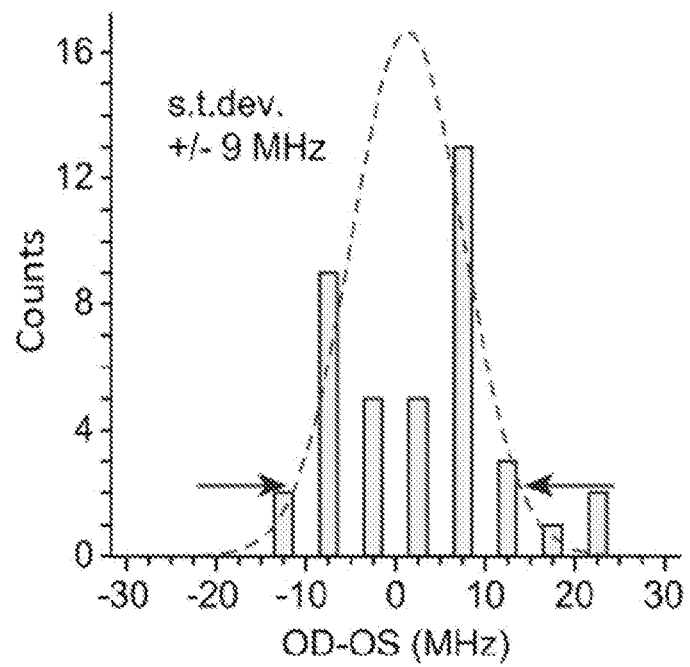
FIG. 12B is a graph that depicts experimental results of the measured central corneal Brillouin frequency shift OD-OS difference of 37 patients.

In another study, the central corneal Brillouin frequency shift OD-OS difference of 37 patients was measured. The results from the two corneas presented a very narrow range, with a difference from two eyes falling in a distribution with a standard deviation of <10 MHz, as is shown in FIG. 12B.

Example 2

A study was conducted to evaluate the efficacy of the systems and methods described herein as well as the effects of diseases that necessitate these solutions.

Keratoconus, a degenerative corneal disease, is one example of an ocular disease that can be evaluated using systems and methods of the present disclosure. The onset of keratoconus is often unilateral. For example, keratoconus can begin with one eye, and thereafter the fellow eye or second eye can start to develop abnormal changes. Brillouin frequency shifts were measured in both eyes of human subjects who had been classified with early mild keratoconus in stage 1 in one eye but whose second eyes were normal according to a standard pachymetry reading and an Amsler-Krumeich Classification. Brillouin biomechanical values measured at central-inferior regions (0.8-1 mm below the optic center) were statistically significantly (p<0.0001, 4 subjects) different between the two eyes. Brillouin values measured at the thinnest region (0.5-1 mm diameter) of the cornea were also significantly different between the two eyes. The Brillouin shift was lower in the stage −1 eye than the normal eye in each subject. By contrast, the differences between two eyes in normal, healthy patients (n=20) were less than the measurement accuracy (+/−10 MHz). This example demonstrates the capability of using the biomechanical difference between left and right eyes for the detection of early keratoconus.

Figure 13:
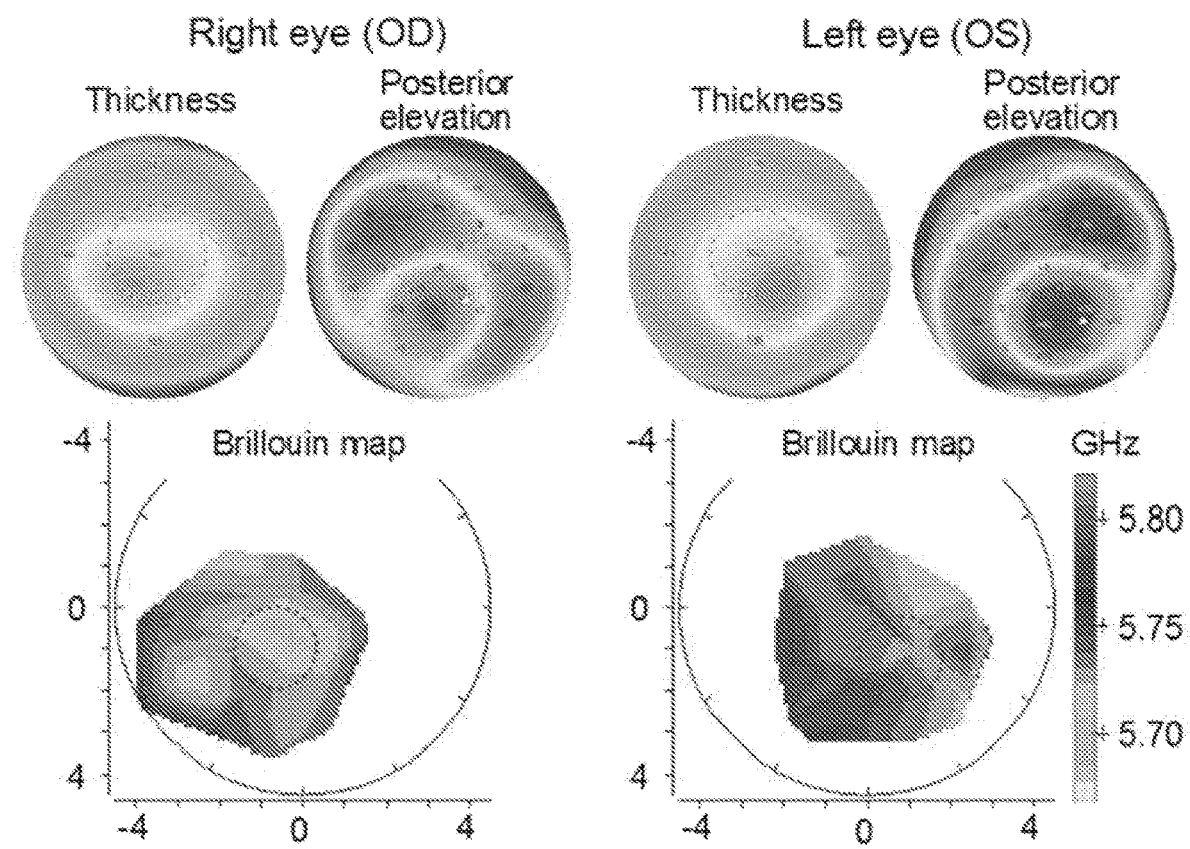
FIG. 13 is a set of maps providing experimental results of measured Brillouin frequency shifts in both eyes of human subjects who had been classified with early mild keratoconus (left set) and normal healthy patients (right set).

In another study, Brillouin frequency shifts were measured in both eyes of human subjects who had been classified with early mild keratoconus in Stage 1 in both eyes according to a standard pachymetry reading and an Amsler-Krumeich Classification. FIG. 13 (left set) shows a typical example from a stage-1 patient. Brillouin biomechanical values measured at the thinnest (cone) region (R<1 mm from thinnest point in the cornea) of the cornea were significantly different between the two eyes (n=4, p<0.0001). The corneal thickness and posterior elevation maps were acquired with a Scheimpflug-based corneal topography system, along with a Brillouin elasticity map of a patients diagnosed with early keratoconus (Stage I) in both eyes (38.5±5.73 y/d, 2 male). Broken line circles denote cone regions R<1 mm around the thinnest point.

By contrast, FIG. 13 (right set) shows the differences between two eyes in normal, healthy patients (n=37) were less than the measurement accuracy (+/−10 MHz). The absolute OD-OS difference in central Brillouin measurements in normal (dots on left side) and eight Stage I keratoconus corneas of four patients (dots on right side). Yellow dots illustrate central difference (R<1 mm from the pupil center). The dots on the right side represent minimum Brillouin measurement difference in the cones of two eyes (***p<0.001). This example demonstrates the feasibility of using the biomechanical difference between left and right eyes for the detection of early keratoconus. Hence, FIG. 13 illustrates the diagnostic efficacy of a Brillouin measurement parameter in keratoconus.

Figure 14:
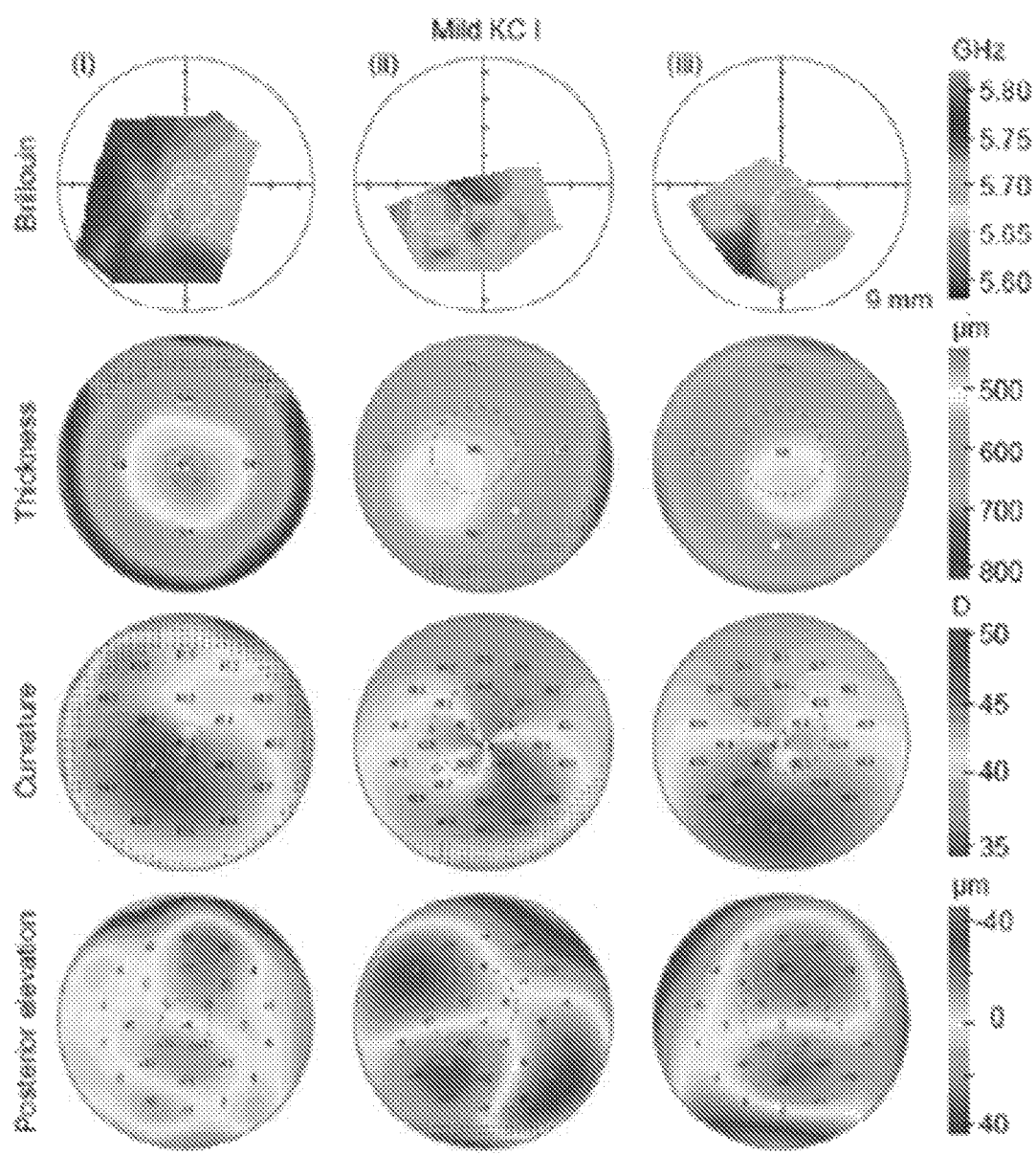
FIG. 14 is a set of maps providing experimental results of measured regional heterogeneity in early stage keratoconus patients.

These successful examples, which are based on comparing the left and right eyes of each subject and comparing regional difference within the same cornea, represent the usefulness of "self-calibration", where the calibration reference is provided by another region in the same eye or the other eye of the subject. Locally compromised elasticity measured with Brillouin spectroscopy has been observed in keratoconus patients in stage III and IV. Regional heterogeneity in early stage keratoconus patients was measured, and the results are depicted in FIG. 14, which shows representative Brillouin images of corneas with Stage I keratoconus. Rows 2-4 are topography images obtained with Scheimpflug-principle-based imaging systems that are commonly used in clinical practice: thickness (um), keratometry (or sagittal curvature, in diopter) and posterior corneal surface elevation (um).

Figure 15A:
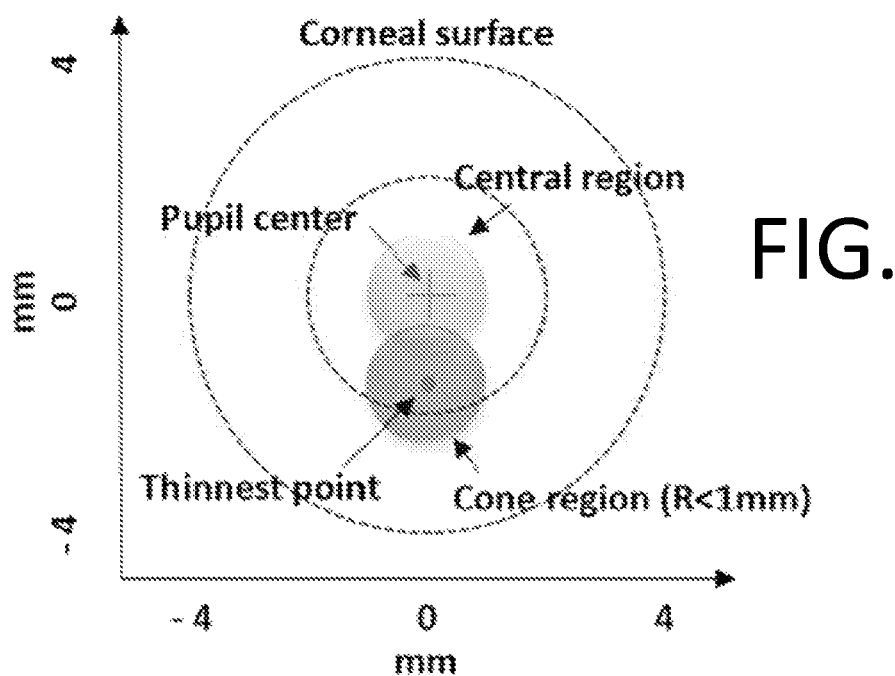
FIG. 15A is a graph that depict regional differences in Brillouin frequency shift measurements on keratoconus corneas.
Figure 15B:
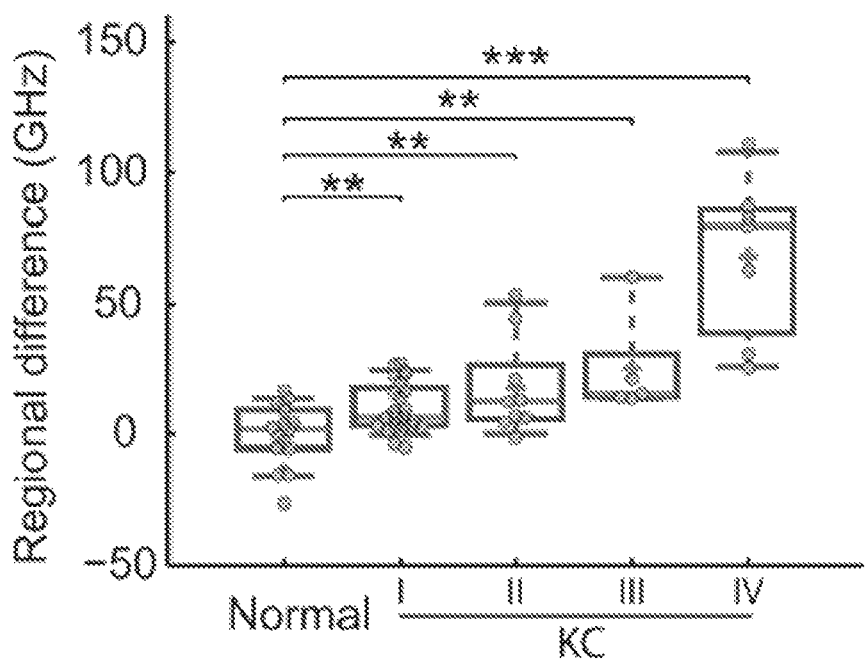
FIG. 15B is a graph that illustrates regional differences in Brillouin measurements in keratoconus corneas from Stage I-IV.

When analyzing data from keratoconus patients from stage I to IV, the Brillouin shift values measured at the cone areas were significantly (P<0.001, paired t-test) lower than the values in the peripheral regions (R>3 mm from the optic axis) in the same eyes, and regional difference increases with severity of the disease, as shown in FIGS. 15A and 15B. By comparison, interpersonal comparison of the Brillouin shift values did not reveal a difference. Brillouin values at the cone regions in keratoconus patients were not distinctly different (p>0.05) from those measured in normal subjects at the central corneas. This insensitivity is largely due to relatively large variability between subjects. FIG. 15A depicts regional differences in Brillouin frequency shift measurements on keratoconus corneas. As illustrated in FIG. 15B, the central region can be defined as <1 mm from pupil center, and the cone region in corneas with keratoconus can be defined as the region <1 mm from thinnest point defined by Scheimpflug corneal topography. FIG. 15B illustrates regional differences in Brillouin measurements in keratoconus corneas from Stage I-IV. The statistical significance was determined by two-sided, unpaired student tests (p<0.01, *p<0.001).

Some Fuchs' dystrophy is associated with the loss of endothelial cell function in water transport. The corneal thickness recovery in response to induced hydration change has been suggested as a test of endothelial function. Brillouin microscopy can be used to measure abnormal hydration changes in patients with Fuchs' dystrophy and help monitor the progression of the disease. Metrics such as minimum Brillouin shift and difference between the minimum (or central) to peripheral Brillouin values can be used to measure the degree of swelling for diagnosis and treatment monitoring of Fuchs' dystrophy.

Some dry eye syndrome is caused by a chronic problem in tear film, which does not provide sufficient lubrication and moisture on the corneal surface. The corneal tissues in dry eye are thought to have lower hydration and therefore higher Brillouin shifts than normal corneas. As such, Brillouin frequency shifts can serve as useful indicator for the diagnosis and treatment monitoring of patients for dry eye.

Some collagen-rich tissues, such as cornea, skin, and muscles, are highly anisotropic, and their biomechanical and optical properties are orientation dependent. It has been found that the Brillouin shift of the cornea is higher by 50-100 MHz when the optical beam is oriented at an angle to the corneal surface, in comparison to the case where the beam enters the cornea perpendicularly to the corneal surface.

In corneal stroma, collagen fibrils form lamellas and they have different orientations in the x-y plane. The Brillouin frequency f measured as a function of the angle θ with respect to the normal to the corneal plane can be expressed by:

$$f \approx f_0 + \Delta f \sin\theta$$

Here $f_0$ is the value measured normal to the cornea, and $\Delta f$ represents axial-asymmetry of the tissue. $\Delta f$ may range from 0 to 1 GHz depending on material. $\Delta f$ of typical corneas is about 200-400 MHz as measured with an optical wavelength of 780 nm.

This asymmetry or frequency difference is measurable by varying the angle of the probe beam axis with respect to the corneal surface normal. For example, the two principle axis values may be measured from two measurements:

$$\begin{pmatrix} f_n \\ f_p \end{pmatrix} = \begin{pmatrix} \cos\theta_1 & \sin\theta_1 \\ \cos\theta_2 & \sin\theta_2 \end{pmatrix}^{-1} \begin{pmatrix} f1 \\ f2 \end{pmatrix}$$

where $f_n$ denotes the Brillouin shift along the axis orthogonal to the corneal surface and $f_p$ denotes the Brillouin shift along the axis parallel to the corneal surface, and f1 and f2 are Brillouin shifts measured with tilt angles, $\theta_1$ and $\theta_2$, respectively.

The effect of water or hydration is spatially isotropic to a large extent and should be independent of Brillouin probe beam angle. Therefore, the hydration does not significantly affect $\Delta f$. Therefore, the axis asymmetry metric represents the mechanical properties of solid-part components, particularly collagen fiber structure. Changes in the thickness, density, and crosslinking of collagen fibrils can manifest themselves in the axis asymmetry metric.

Because two or multiple measurements of the same cornea are made, the contribution from homogeneous confounding factors can be canceled out. Therefore, the anisotropic factor represented by the angular difference can be a sensitive metric for the monitoring of corneal health and diagnosis of corneal disease.

Myopia is related to eyeball deformation and elongation, because of a weaker, more extensible sclera, with the inability to withstand the expansive forces of the intraocular pressure. The sclera is a tough shell to protect and support the more delicate intraocular structure. Studies have confirmed the ultrastructural alteration, tissue loss, and biomechanical remodeling in sclera of myopic eyes. In myopic eyes, the scleral thickness and cross-sectional areas at the equator, midpoint between equator and posterior pole, optic nerve head border, and posterior pole decrease significantly with axial length of the eyeball. Because sclera remodeling is triggered on site when myopia is started, a regional decrease in elasticity of these areas may be used to predict pathological myopia. This can be quantified with the Brillouin imaging systems and method described herein.

Crosslinking is a medical procedure that can be used to treat corneal ectasia and abnormal eye growth (e.g. leading to myopia) by stiffening the cornea or sclera. Crosslinking can be achieved by applying dyes, such as riboflavin and rose bengal, and light to ocular tissue. Related exemplary crosslinking techniques are discussed in U.S. Patent Publication No. 2016/0151202, the contents of which are incorporated herein by reference. Brillouin frequency shifts can be measured at various regions where varying degrees of crosslinking may be induced, and the difference in Brillouin values between the regions can provide information to confirm whether the procedure was done appropriately or efficiently. For example, the cone region in a keratoconus patient can be illuminated with a higher intensity of UVA light whereas the peripheral region can be illuminated with lower intensity of UVA light. The regional difference, particularly in comparison to the regional difference measured prior to the crosslinking procedure, can be calculated. The difference is expected to increase after crosslinking. Otherwise, no change or less change than expected indicates that the procedure may not have been effective. In scleral crosslinking, the difference in Brillouin frequency shifts between the equatorial sclera and anterior sclera can be measured before and after crosslinking. Relatedly, the change in the regional difference can also be used as a metric to assess the efficiency of crosslinking.

Another example is myopic anisometropia, where the two eyes of an individual, with an identical biological background and primarily subject to the same environmental factors, can develop significantly different refractive errors. Anisometropia can be characterized by intraocular asymmetry. Studies suggest the intraocular asymmetry is related to the magnitude or rate of posterior ocular growth. This suggests distinct structural and biomechanical developments in the two eyes, and therefore characterization of the difference in the same regions of the two eyes on sclera, for example, the equator regions, can potentially help identify early anisometropia for early intervention.

Figure 16:
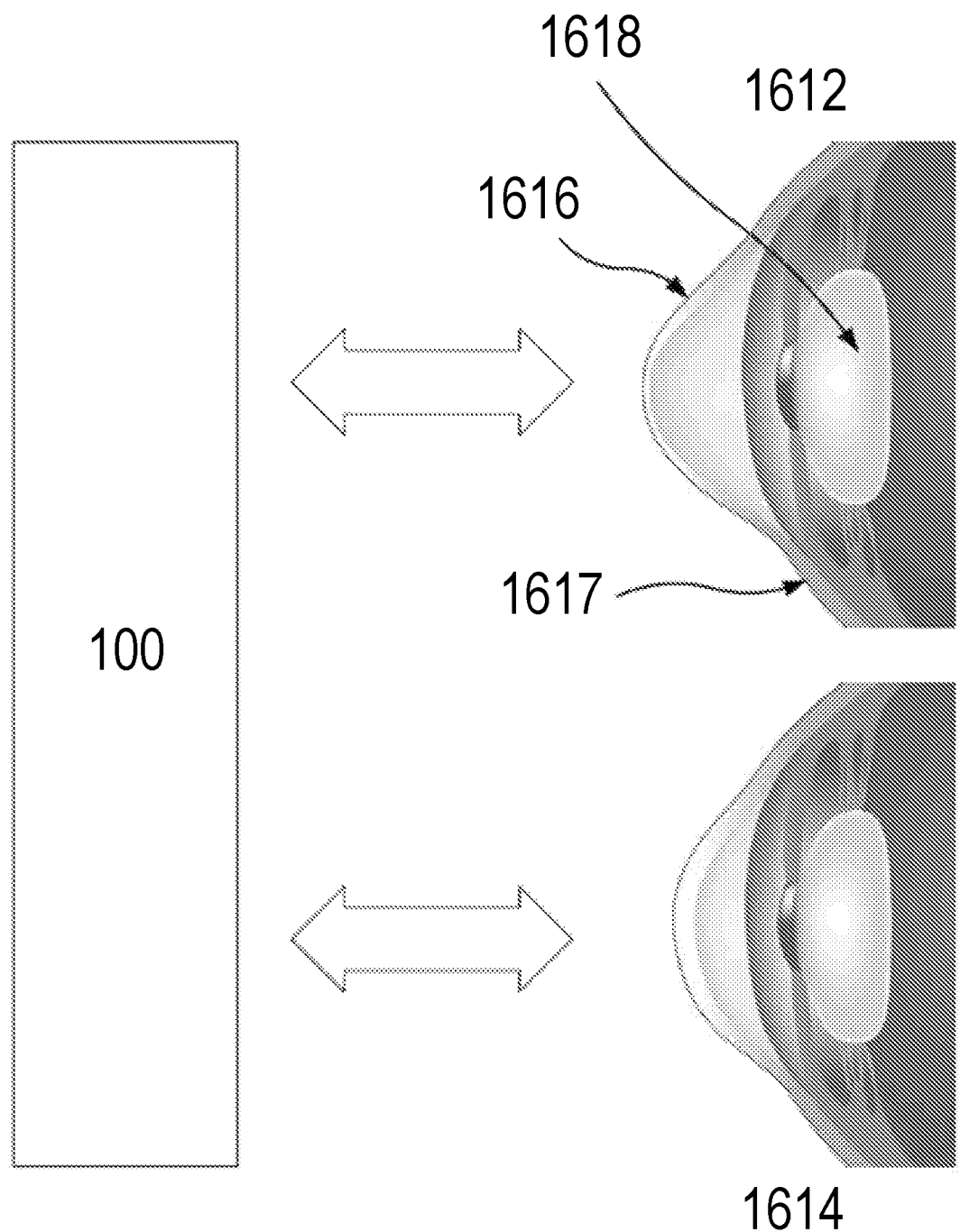
FIG. 16 is a diagram illustrating tissue a evaluation system in accordance with the present disclosure that can be configured to obtain a first biomechanical value for the tissue of an eye of a patient.

FIG. 16 depicts aspects of a Brillouin imaging system 100 according to the aspects of the present disclosure. The tissue evaluation system 100 can include optical coherence tomography (OCT) modalities, Brillouin imaging modalities, Raman imaging modalities, laser speckle imaging modalities, multi-photon imaging modalities, photo-acoustic imaging modalities, confocal microscopy imaging modalities, fluorescence imaging modalities, Pentacam imaging modalities, ultrasound imaging modalities, as well as assemblies that combine or include one or more of these imaging modalities. Relatedly, exemplary tissue evaluation or assessment techniques that can be used in conjunction with the tissue evaluation system 100 can include those described in U.S. Pat. Nos. 7,898,656, 8,115,919, and 9,777,053, and U.S. Patent Publication Nos. 2012/0302862 and 2016/0151202, the contents of which are incorporated herein by reference.

As shown in FIG. 16, tissue evaluation system 100 can be configured to obtain a first biomechanical value for the tissue of an eye 1612 of the patient. The system 100 can also be configured to obtain a second biomechanical value for the other eye 1614 (e.g. the second eye) of the patient. Further, system 100 can be configured to compare the first biomechanical value with the second biomechanical value to evaluate the tissue of the eye. As shown here, eye 1612 is a keratoconus eye and the second eye 1614 is a normal or healthy eye. In some cases, the first biomechanical value is an elasticity value for the tissue of the eye, and the second biomechanical value is an elasticity value for the corresponding tissue of the second eye. In some cases, the tissue is corneal tissue 1616. In some cases, the tissue is sclera tissue 1617. In some cases, the tissue is lens tissue 1618. In some cases, the first biomechanical value is obtained with Brillouin spectroscopy. In some cases, the first biomechanical value is obtained with Brillouin microscopy. In some cases, the first biomechanical value is obtained with an air-puff based optical imaging technique. An air-puff based optical imaging technique can be, for example, a Scheimpflug topography technique or an optical coherence tomography technique. In some cases, the first biomechanical value for the tissue of the eye of the patient can be obtained at a central inferior corneal region of the eye, and the second biomechanical value for the corresponding tissue of the second eye of the patient can be obtained at a central inferior corneal region of the second eye. In some cases, the first biomechanical value for the tissue of the eye of the patient can be obtained at the thinnest corneal region of the eye, and the second biomechanical value for the corresponding tissue of the second eye of the patient can be obtained at the thinnest corneal region of the second eye. Although FIG. 16 depicts a binocular tissue evaluation technique, embodiments of the present invention encompass monocular tissue evaluation techniques as discussed elsewhere herein.

According to exemplary embodiments of the present invention, systems and methods can be used to perform a Brillouin microscopy in ocular tissue in vivo, which can be valuable in ocular biomechanical characterization in diagnosing and treating ocular problems, as well as developing novel drugs or treatments.

There are four anatomical sites in the eye. For example, the cornea is a thin (e.g., less than 1 mm) tissue composed of different layers of varying mechanical strength. The aqueous humor is a liquid with similar properties to water that fills the anterior chamber of the eye. The crystalline lens is a double-convex sphere composed by many layers of different index of refraction, density and stiffness. The vitreous humor is the viscous transparent liquid that fills the posterior chamber of the eye.

Brillouin light scattering in a tissue or any other medium usually arises due to the interaction between an incident light and acoustic waves within the matter. For example, a probe light having a frequency v and a wavelength λ can be used, which may be provided to a sample. In a Spontaneous Brillouin process, the acoustic waves or acoustic phonons are naturally present due to thermal fluctuations. Such fluctuations propagate through the medium in the form of acoustic waves. These acoustic waves can generate periodic modulations of the refractive index. Brillouin scattering can be generated by at least one or many acoustic waves or acoustic phonons, which form phase-matched index modulation.

All patent filings, scientific journals, books, treatises, and other publications and materials discussed in this application are hereby incorporated by reference for all purposes. A variety of modifications are possible within the scope of the present invention. A variety of parameters, variables, factors, and the like can be incorporated into the exemplary method steps or system modules. While the specific embodiments have been described in some detail, by way of example and for clarity of understanding, a variety of adaptations, changes, and modifications will be obvious to those of skill in the art.

All features of the described systems and/or devices are applicable to the described methods mutatis mutandis, and vice versa. Each of the calculations discussed herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing the method steps described herein. Suitable tangible media may comprise a memory (including a volatile memory and/or a non-volatile memory), a storage media (such as a magnetic recording on a floppy disk, a hard disk, a tape, or the like; on an optical memory such as a CD, a CD-R/W, a CD-ROM, a DVD, or the like; or any other digital or analog storage media), or the like. While the exemplary embodiments have been described in some detail, by way of example and for clarity of understanding, those of skill in the art will recognize that a variety of modification, adaptations, and changes may be employed.

The methods and apparatuses of the present disclosure may be provided in one or more kits for such use. The kits may comprise a system or device for evaluating a patient tissue and instructions for use. Optionally, such kits may further include any of the other system components described in relation to the present invention and any other materials or items relevant to the present invention. The instructions for use can set forth any of the methods as described above.

The present invention has been described in terms of one or more preferred embodiments, and it should be appreciated that many equivalents, alternatives, variations, and modifications, aside from those expressly stated, are possible and within the scope of the invention.

The invention claimed is:

1. A Brillouin spectroscopy system for evaluating a tissue in an eye tissue region of a patient, the system comprising:
   a laser source system comprising:
      a tunable laser source configured to produce a first electromagnetic radiation having an electromagnetic spectrum; and
      a vapor cell-based reference configured to capture a portion of the first electromagnetic radiation and provide an error signal containing information about a deviation of the electromagnetic spectrum from a target electromagnetic spectrum, the vapor cell-based reference comprising:
         a vapor cell filter configured to receive the portion of the first electromagnetic radiation and selectively transmit the portion of the first electromagnetic radiation based on the electromagnetic spectrum; and
         a detector configured to receive the transmitted portion of the first electromagnetic radiation and produce the error signal for use in controlling the tunable laser source;
   a human interface configured to direct the first electromagnetic radiation to the eye tissue region of the patient, wherein the first electromagnetic radiation interacts with at least one acoustic wave intrinsic to the eye tissue region and at least one second electromagnetic radiation is produced based on the at least one acoustic wave;
   vapor absorption filter configured to receives the first electromagnetic radiation and the second electromagnetic radiation and transmit the second electromagnetic radiation, while attenuating the first electromagnetic radiation; and
   a spectrometer system configured to receive a portion of the second electromagnetic radiation from the vapor absorption filter and provide information associated with a biomechanical property of the eye tissue region.

2. The Brillouin spectroscopy system of claim 1, wherein the target electromagnetic spectrum is a wavelength of an absorption line of an atomic species.

3. The Brillouin spectroscopy system of claim 2, wherein the target electromagnetic spectrum is a wavelength of a Rubidium absorption line.

4. The Brillouin spectroscopy system of claim 3, wherein the target electromagnetic spectrum is a wavelength of 780 nm.

5. The Brillouin spectroscopy system of claim 3, wherein the target electromagnetic spectrum is a wavelength of 780 nm.

6. The Brillouin spectroscopy system of claim 1, further comprising a spectral cleanup filter configured to provide a second error signal containing information about the spectral noise within the first electromagnetic radiation.

7. The Brillouin spectroscopy system of claim 1, wherein the human interface comprises a fiber-optic probe.

8. The Brillouin spectroscopy system of claim 7, wherein the fiber-optic probe forms at least one of a catheter or a pen endoscope.

9. The Brillouin spectroscopy system of claim 1, further comprising a computer system in communication with the human interface and the spectrometer system and configured to obtain a first biomechanical value for a first eye tissue region of a patient, obtain a second biomechanical value for a second eye tissue region of the patient, and determine a medical condition of the tissue of the eye of the patient by comparing the first biomechanical value with the second biomechanical value.

10. The Brillouin spectroscopy system of claim 9, wherein the computer system is further configured to assess an axial-asymmetry between the first eye tissue region and the second eye tissue region to determine the medical condition.

11. The Brillouin spectroscopy system of claim 10, wherein the computer system is further programmed to determine a Brillouin frequency, f, measured as a function of an angle, θ, relative to normal on the first eye tissue region and the second eye tissue region, respectively.

12. The Brillouin spectroscopy system of claim 11, wherein the Brillouin frequency is given by:

$$f \approx f_\theta + \Delta f \sin \theta$$

where $f_\theta$ is a value measured normal to the first eye tissue region or the second eye tissue region and Δf is the axial-asymmetry between the first eye tissue region and the second eye tissue region.

13. A laser source system for creating a laser with a stabilized peak frequency and filtered spontaneous emission noise, the laser source system comprising:
   a tunable laser source configured to produce a first electromagnetic radiation having an electromagnetic spectrum; and
   a vapor cell-based reference configured to capture a polarized form of a portion of the first electromagnetic radiation and provide an error signal containing information about a deviation of the electromagnetic spectrum from a target electromagnetic spectrum, the vapor cell-based reference comprising:
      a first polarizer configured to receive and change the polarity of the portion of the first electromagnetic radiation;
      a vapor cell configured to receive the polarized form of the portion of the first electromagnetic radiation from the first polarizer;
      a second polarizer configured to receive the polarized form of the portion of the first electromagnetic radiation from the vapor cell and change the polarity of the portion of the first electromagnetic radiation; and
      a detector configured to receive the polarized form of the portion of the first electromagnetic radiation from the second polarizer and produce the error signal; and
   a spectral cleanup filter configured to:
      provide a second error signal containing information about the spectral noise within the first electromagnetic radiation;
      filter at least a portion of the spectral noise; or
         include two tandem Fabry-Perot (FP) cavities, wherein each cavity is formed from a pair of concave mirrors.

14. The laser source system of claim 13, wherein the target electromagnetic spectrum is at least one of a wavelength of a Rubidium absorption line or a wavelength of 780 nm.

15. The laser source system of claim 13, wherein the laser source system is configured to be coupled to:
   a human interface configured to direct the first electromagnetic radiation to the eye tissue region of the patient, wherein the first electromagnetic radiation interacts with at least one acoustic wave intrinsic to the eye tissue region and at least one second electromagnetic radiation is produced based on the at least one acoustic wave; and
   a spectrometer system configured to receive a portion of the second electromagnetic radiation and provide information associated with a biomechanical property of the eye tissue region.

16. The laser source system of claim 15, wherein the human interface comprises at least one of:
   a fiber-optic probe;
   a catheter; and
   a pen endoscope.

17. The laser source system of claim 15, wherein the laser source system is configured to be coupled to a computer system in communication with the human interface and the spectrometer system and configured to obtain a first biomechanical value for a first eye tissue region of a patient, obtain a second biomechanical value for a second eye tissue region of the patient, and determine a medical condition of the tissue of the eye of the patient by comparing the first biomechanical value with the second biomechanical value.

18. The laser source system of claim 17, wherein the computer system is further configured to assess an axial-asymmetry between the first eye tissue region and the second eye tissue region to determine the medical condition.

19. The laser source system of claim 18, wherein the computer system is further programmed to determine a Brillouin frequency, f, measured as a function of an angle, θ, relative to normal on the first eye tissue region and the second eye tissue region, respectively.

20. A method of evaluating a tissue in an eye of a patient, the method comprising:
   obtaining a first biomechanical value for a first eye tissue region of the patient using Brillouin spectroscopy;
   obtaining a second biomechanical value for a second eye tissue region of the patient;
   comparing the first biomechanical value with the second biomechanical value to determine a medical condition of the tissue of the eye of the patient; and
   wherein the second biomechanical value is obtained with an air-puff based optical imaging technique.

21. The method of claim 20, wherein comparing the first biomechanical value with the second biomechanical value includes assessing an axial-asymmetry between the first eye tissue region and the second eye tissue region to determine the medical condition.

22. The method of claim 21, wherein obtaining a first biomechanical value and obtaining a second biomechanical value includes determining a Brillouin frequency, f, measured as a function of an angle, θ, relative to normal on the first eye tissue region and the second eye tissue region, respectively.

23. The method of claim 22, wherein the Brillouin frequency is given by:

$$f \approx f_\theta + \Delta f \sin \theta$$

where $f_\theta$ is a value measured normal to the first eye tissue region or the second eye tissue region and Δf is the axial-asymmetry between the first eye tissue region and the second eye tissue region.

24. The method of claim 20, wherein the comparing includes determining differences in elasticity within a cornea of the patient.

25. The method of claim 20, wherein the medical condition includes keratoconus.

26. The method of claim 20, wherein the first tissue region and the second tissue region are located on the eye of the patient.

27. The method of claim 20, wherein the first biomechanical value is an elasticity value for the first tissue region of the eye, and wherein the second biomechanical value is an elasticity value for the second tissue region of the eye.

28. The method of claim 20, wherein the first tissue region is located on the eye of the patient and the second tissue region is located on a second eye of the patient.

29. The method of claim 20, wherein the first biomechanical value is at least one of:
- an elasticity value for the first tissue region of the eye, and wherein the second biomechanical value is an elasticity value for the corresponding tissue region of a second eye;
- for the tissue of the eye of the patient and is obtained at a central inferior corneal region of the eye, and wherein the second biomechanical value for the corresponding tissue of the second eye of the patient is obtained at a central inferior corneal region of the second eye;
- for the tissue of the eye of the patient and is obtained at the thinnest corneal region of the eye, and wherein the second biomechanical value for the corresponding tissue of the second eye of the patient is obtained at the thinnest corneal region of the second eye.

30. The method of claim 20, wherein the first tissue region comprises a member selected from the group consisting of a corneal tissue, a sclera tissue, and a lens tissue.

31. The method of claim 20, wherein the second tissue region comprises a member selected from the group consisting of a corneal tissue, a sclera tissue, and a lens tissue.

32. The method of claim 20, wherein the second biomechanical value is obtained with Brillouin microscopy.

33. The method of claim 20, wherein the air-puff based optical imaging technique is selected from the group consisting of Scheimpflug topography and optical coherence tomography.

34. A Brillouin spectroscopy system for evaluating a tissue in an eye tissue region of a patient, the system comprising:
- a laser source system comprising:
  - a tunable laser source configured to produce a first electromagnetic radiation having an electromagnetic spectrum; and
  - a vapor cell-based reference configured to capture a portion of the first electromagnetic radiation and provide an error signal containing information about a deviation of the electromagnetic spectrum from a target electromagnetic spectrum, wherein the error signal is produced by monitoring the absorption of the first electromagnetic radiation by atoms within the vapor cell-based reference;
- a human interface configured to direct the first electromagnetic radiation to the eye tissue region of the patient, wherein the first electromagnetic radiation interacts with at least one acoustic wave intrinsic to the eye tissue region and at least one second electromagnetic radiation is produced based on the at least one acoustic wave; and
- a spectrometer system configured to receive a portion of the second electromagnetic radiation and provide information associated with a biomechanical property of the eye tissue region; and
- a spectral cleanup filter configured to provide a second error signal containing information about the spectral noise within the first electromagnetic radiation.

35. The Brillouin spectroscopy system of claim 34, wherein the target electromagnetic spectrum is at least one of a wavelength of an absorption line of an atomic species or a wavelength of a Rubidium absorption line.

36. The Brillouin spectroscopy system of claim 34, wherein the human interface comprises a fiber-optic probe.

37. The Brillouin spectroscopy system of claim 36, wherein the fiber-optic probe forms a catheter or a pen endoscope.

38. The Brillouin spectroscopy system of claim 34, further comprising a computer system in communication with the human interface and the spectrometer system and configured to obtain a first biomechanical value for a first eye tissue region of a patient, obtain a second biomechanical value for a second eye tissue region of the patient, and determine a medical condition of the tissue of the eye of the patient by comparing the first biomechanical value with the second biomechanical value.

39. The Brillouin spectroscopy system of claim 38, wherein the computer system is further configured to assess an axial-asymmetry between the first eye tissue region and the second eye tissue region to determine the medical condition.

40. The Brillouin spectroscopy system of claim 39, wherein the computer system is further programmed to determine a Brillouin frequency, f, measured as a function of an angle, θ, relative to normal on the first eye tissue region and the second eye tissue region, respectively.

41. The Brillouin spectroscopy system of claim 40, wherein the Brillouin frequency is given by:

$f \approx f_\theta + \Delta f \sin\theta$ where $f_\theta$ is a value measured normal to the first eye tissue region or the second eye tissue region and $\Delta f$ is the axial-asymmetry between the first eye tissue region and the second eye tissue region.

42. The Brillouin spectroscopy system of claim 34, wherein the error signal is produced by providing a modulation to the first electromagnetic radiation.

43. The Brillouin spectroscopy system of claim 34, further comprising at least one polarizer and at least one source of a magnetic field, wherein the error signal is produced by from the polarization-dependence of atomic absorption in the magnetic field.

* * * * *

UNITED STATES PATENT AND TRADEMARK OFFICE
CERTIFICATE OF CORRECTION

| | | |
|---|---|---|
| PATENT NO. | : 11,576,571 B2 | |
| APPLICATION NO. | : 16/639962 | |
| DATED | : February 14, 2023 | |
| INVENTOR(S) | : Seok-Hyun Yun et al. | |

It is certified that error appears in the above-identified patent and that said Letters Patent is hereby corrected as shown below:

In the Specification

Column 1, Line 18, should be --This invention was made with government support under EY025454 awarded by the National Institutes of Health. The government has certain rights in the invention--.

Signed and Sealed this
Second Day of May, 2023

Katherine Kelly Vidal
*Director of the United States Patent and Trademark Office*